(12) United States Patent
Delhomel et al.

(10) Patent No.: US 8,188,148 B2
(45) Date of Patent: May 29, 2012

(54) SUBSTITUTED 1,3-DIPHENYLPROPANE DERIVATIVES, PREPARATIONS AND USES THEREOF

(75) Inventors: Jean-François Delhomel, Acq (FR); Rémy Hanf, Lille (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 479 days.

(21) Appl. No.: 12/308,558

(22) PCT Filed: Jun. 21, 2007

(86) PCT No.: PCT/EP2007/056225
§ 371 (c)(1),
(2), (4) Date: Dec. 18, 2008

(87) PCT Pub. No.: WO2007/147880
PCT Pub. Date: Dec. 27, 2007

(65) Prior Publication Data
US 2010/0286276 A1 Nov. 11, 2010

(30) Foreign Application Priority Data
Jun. 21, 2006 (FR) .................................. 06 05540

(51) Int. Cl.
| | |
|---|---|
| *A01N 37/10* | (2006.01) |
| *A61K 31/19* | (2006.01) |
| *C07C 321/00* | (2006.01) |
| *C07C 323/00* | (2006.01) |
| *C07C 381/00* | (2006.01) |
| *C07C 59/90* | (2006.01) |
| *C07C 62/32* | (2006.01) |
| *C07C 65/40* | (2006.01) |
| *C07C 59/56* | (2006.01) |
| *C07C 59/88* | (2006.01) |
| *C07C 65/00* | (2006.01) |

(52) U.S. Cl. ......... 514/571; 562/431; 562/464; 562/472
(58) Field of Classification Search .................. 514/571; 562/431, 464, 472
See application file for complete search history.

(56) References Cited

FOREIGN PATENT DOCUMENTS
| | | | |
|---|---|---|---|
| CA | 2169187 A1 * | 2/1995 | |
| DE | 2 149 070 | 4/1973 | |
| DE | 41 21 849 | 1/1993 | |
| DE | 43 27 365 | 2/1995 | |

OTHER PUBLICATIONS

Vippagunta et al. Advanced Drug Delivery Reviews, 2001, vol. 48, pp. 3-26.*
Morishita et al., "Synthesis and Hypolilidaemic Activity of 2-Substituted Isobutyric Acid Derivatives" Journal of Medicinal Chemistry, American Chemical Society. Washington, US, vol. 31, No. 6, Jun. 1988, pp. 1205-1209, XP002003702.
Labaudiniere et al., "Omega-[(Omega-Arylalkyl) ARYL]Alkanoic Acids: A New Class of Specific LTA4 Hydrolase Inhibitors", Journal of Medicinal Chemistry, American Chemical Society. Washington, US, vol. 35, No. 17, 1992, pp. 3156-3169, XP001205195.
Database CA, Chemical Abstracts Service, Columbus, Ohio, US; He, Lan et al., "Synthesis and Biological Activity of Flavane Derivatives", XP002425766, 2006.
International Search Report for PCT/EP2007/056225, mailed Oct. 29, 2007.

* cited by examiner

*Primary Examiner* — Samira Jean-Louis
(74) *Attorney, Agent, or Firm* — Nixon & Vanderhye P.C.

(57) ABSTRACT

The present invention concerns substituted 1,3-diphenylpropane derivatives, pharmaceutical compositions comprising them and the therapeutic uses thereof, particularly in the field of human and animal health.

7 Claims, 16 Drawing Sheets

SUBSTITUTED 1,3-DIPHENYLPROPANE DERIVATIVES, PREPARATIONS AND USES THEREOF

Figure 1:
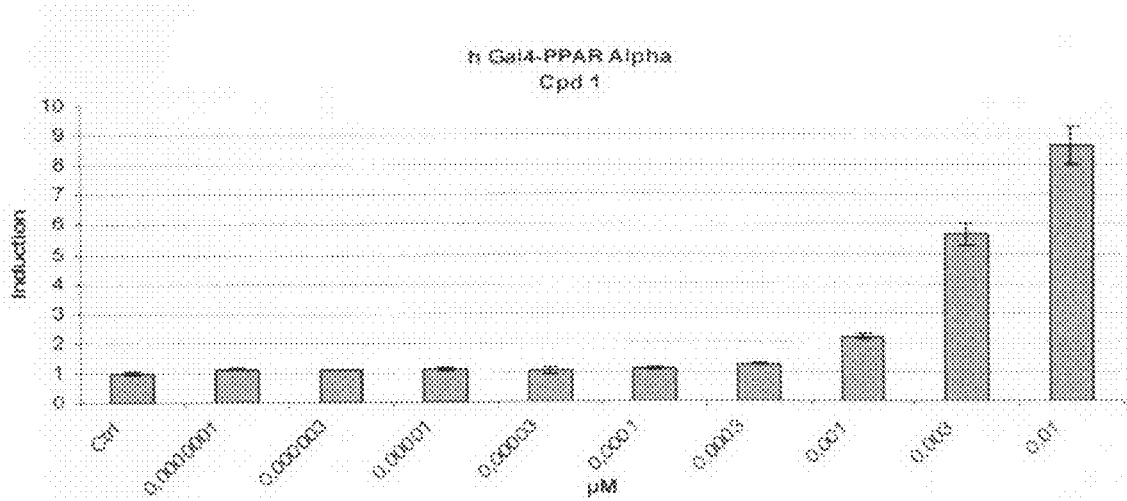

This application is the U.S. national phase of International Application No. PCT/EP2007/056225, filed 21 Jun. 2007 which designated the U.S. and claims priority to French Application No. 0605540, filed Jun. 21, 2006, the entire contents of each of which are hereby incorporated by reference.

The present invention relates to substituted 1,3-diphenylpropane derivatives, pharmaceutical compositions comprising them and the therapeutic uses thereof, in particular in the fields of human and animal health.

The inventors have shown, surprisingly, that the compounds according to the present invention have intrinsic PPAR agonist properties.

The molecules described in this invention are therefore of particular interest in the treatment of metabolic syndrome complications, insulin resistance, diabetes, dyslipidemias, atherosclerosis, cardiovascular disease, obesity, hypertension, inflammatory diseases (asthma, etc.), neurodegenerative diseases (Alzheimer's disease, etc.), cancer, etc., as well as reducing the global risk. The compounds according to this invention are to be used preferably for treating dyslipidemias.

Diabetes, obesity, and dyslipidemias (high plasma LDL-cholesterol and triglycerides levels, low HDL-cholesterol levels, etc.) are some of the clearly-identified cardiovascular risk factors which may predispose a person to develop cardiovascular diseases (Mensah M, 2004). Also to be considered are lifestyle risk factors such as tobacco use, a sedentary lifestyle, and an unbalanced diet. These factors have a synergetic effect: the simultaneous presence of several of these factors dramatically increases cardiovascular risk. Therefore, a global risk of cardiovascular disease deserves to be addressed. In 2004, the prevalence rate of dyslipidemias reached 43.6% of the population in industrialized countries. The sharp increase of diabetics is currently making diabetes an ever more important factor in the epidemiology of cardiovascular diseases: it is estimated that, by 2010, 7.6% of the population will be diabetic (Fox-Tucker J, 2005).

According to the International Atherosclerosis Society (International Atherosclerosis Society, 2003), cardiovascular disease is the primary cause of death in industrialized countries and is becoming ever more prevalent in developing countries. The principal cardiovascular diseases are heart disease, cerebral ischemia, and peripheral arterial diseases.

These data therefore justify taking vigorous measures to significantly reduce cardiovascular morbidity and mortality rates and reveal the necessity of finding effective treatments, in conjunction with life style modification. Taking into account the risk factors for cardiovascular diseases and their consequences, his is a worldwide emergency.

The compounds according to the invention, because of their PPAR agonist properties, are of particular interest for the treatment of pathologies related to deregulations of lipid and/or glucid metabolism, such as diabetes, obesity, dyslipidemias, or inflammation, as well as for reducing the global cardiovascular risks.

PPARs ($\alpha$, $\gamma$, and $\delta$) are known to be involved in this type of pathologies (Kota B P et al., 2005): ligands and receptors are therefore marketed for treatment of these pathologies (Lefebvre P et al., 2006) and various PPAR modulators, agonist or antagonist, selective or non-selective, are currently in high development. A PPAR modulator having advantageous effects on insulin resistance, obesity, dyslipidemias, hypertension, and/or inflammation could be used in the treatment of metabolic syndrome (or syndrome X) (Liu Y and Miller A, 2005).

The family of PPARs includes three isoforms, known as $\alpha$, $\gamma$ and $\delta$ (also known as $\beta$), each being coded by a different gene. These receptors belong to the nuclear receptor and transcription factor superfamily which are activated upon contact with certain fatty acids and/or their lipid metabolites. Activated PPARs form heterodimers with 9-cis retinoic acid receptors (RXR or Retinoid X Receptor) and bind to specific response elements (PPRE or Peroxisome Proliferator Response Element) of the promoter of target genes, thus allowing a control of the transcription.

PPAR$\alpha$ controls lipid metabolism (hepatic and muscular) and homeostasis of glucose, influences intracellular metabolism of lipids and glucids by controlling directly the transcription of genes coding for proteins involved in lipid homeostasis, has anti-inflammatory and antiproliferative effects, and prevents pro-atherogenic effects of the accumulation of cholesterol in macrophages by stimulating cholesterol efflux (Lefebvre P, Chinetti G, Fruchart J C and Staels B, 2006). Fibrates (fenofibrate, bezafibrate, ciprofibrate, gemfibrozil), via PPAR$\alpha$, are used in clinical medicine to treat certain dyslipidemias by lowering triglycerides and raising HDL (High Density Lipoprotein) levels.

PPAR$\gamma$ is a key regulator of adipogenesis. Additionally, it is involved in lipid metabolism of mature adipocytes, glucose homeostasis, and especially insulin resistance, inflammation, macrophage cholesterol accumulation, and cellular proliferation (Lehrke M and Lazar M A, 2005). Therefore, PPAR$\gamma$ plays a role in the pathogenesis of obesity, insulin resistance, and diabetes. Thiazolidinediones (Rosiglitazone, Troglitazone, etc.) are PPAR$\gamma$ ligands used in the treatment of type 2 diabetes.

There are PPAR$\delta$ ligands (L-165041, GW501516 currently in clinical development), but no PPAR$\delta$ ligand is currently being used as a drug. This receptor is, however, an attractive goal for the development of useable drugs for treatment of dyslipidemias, atherosclerosis, obesity, and insulin resistance: PPAR$\delta$ is in fact involved in lipid and carbohydrate metabolism control, energy balance, neurodegeneration, obesity, formation of macrophage foam cells, and inflammation (Gross B et al., 2005).

Beyond the direct role PPAR ligands play in the regulation of lipid and glucid metabolism, these molecules have a pleiotropic action spectrum due to the great diversity of PPAR target genes. These multiple properties make PPARs interesting therapeutic targets regarding the treatment of diseases such as atherosclerosis, cerebral ischemia, hypertension, diseases connected to neovascularisation (retinopathy, diabetes, etc.), inflammatory and auto-immune diseases (Crohn's disease, psoriasis, multiple sclerosis, asthma, etc.), neoplastic diseases (carcinogenesis, etc.), neurodegenerative diseases, complications associated with metabolic syndrome, insulin resistance, diabetes, dyslipidemias, cardiovascular disease, obesity, etc., as well as for reducing the global risk.

The compounds according to the invention, because of their PPAR agonist properties, are an advantageous therapeutic tool for improving the treatment of pathologies related to a deregulation of lipid and/or glucid metabolism, especially dyslipidemias, as well as reducing the global cardiovascular risk.

More generally, by acting simultaneously on several regulation processes, the compounds according to the invention are an advantageous therapeutic means for the treatment of complications associated with metabolic syndrome (the features of which are obesity, in particular abdominal obesity, an abnormal concentration of blood lipids (high triglyceride level and/or low HDL-cholesterol level (dyslipidemias)), hyperglycemia and/or insulin resistance, and hypertension), atherosclerosis, cardiovascular disease, insulin resistance, obesity, hypertension, diabetes, dyslipidemias, cardiovascular disease, inflammatory disease (asthma, etc.), neurodegenerative pathologies (Alzheimer's disease, etc.), cancer, etc., as well as reducing global risk.

The present invention is directed to compounds, derived from 1,3-diphenylpropane, having the following general formula:

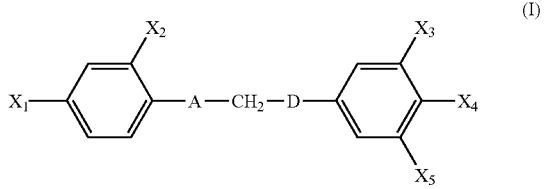

(I)

in which:
X1 represents a halogen atom, a R1 or G1-R1 group;
X2 represents a halogen atom, a R2 or G2-R2 group;
X3 represents a R3 or G3-R3 group;
X4 represents a halogen atom, a R4 or G4-R4 group;
X5 represents a R5 or G5-R5 group;
R1 representing a halogenated alkyl group;
R2 representing a hydrogen atom or a non-halogenated alkyl group;
R3, R4, and R5, identical or different, representing an atom of hydrogen or a substituted alkyl group or not by one or several group 1 or group 2 substituents;
G1, G2, G3, G4, and G5, identical or different, representing an atom of oxygen or sulfur;
with at least one group among X3, X4 or X5 corresponding to a R3, G3R3, R4, G4R4, R5 or G5R5 formula, in which:
G3, G4, and G5 being such as previously described, and
R3, R4, and R5, identical or different, representing an alkyl group substituted by one or several group 1 or group 2 substituents;
A Represents:
  (i) a —CR6R7 group, in which:
    R6 represents a hydrogen atom, an alkyl group, or a —OR8 group and R7 represents an alkyl group, a hydroxyl group, or a —OR8 group, R8 as defined below,
  (ii) a carbonyl group (CO),
  (iii) an oxime group (C=N—O—H) or oxime ether (C=N—O—R8),
    R8, identical or different, representing an alkyl group, substituted or not by an aryl or cycloalkyl group;
D Represents:
  (i) a carbon atom linked to two hydrogen atoms (CH$_2$),
  (ii) a carbon atom linked to a hydrogen atom and to a G2 so as to form an oxygenated or sulfured heterocycle;
substituents of group 1 are chosen among —COOR9 and —CONR9R10;
substituents of group 2 are chosen among —SO$_3$H and —SO$_2$NR9R10;
R9 and R10, identical or different, representing an atom of hydrogen or an alkyl radical substituted or not by at least one group 1 or group 2 substituent;
their stereoisomers (diastereoisomers, enantiomers), pure or mixed, racemic mixtures, geometrical isomers, tautomers, salts, hydrates, solvates, solid forms as well as their mixtures.

In the context of this invention, the term "alkyl" designates a hydrocarbon radical that is saturated, linear, branched, or cyclic, halogenated or not, having particularly from 1 to 24, and preferably 1, 2, 3, 4, 5, 6, 7, 8, 9, or 10, carbon atoms Such as methyl, trifluoromethyl, ethyl, n-propyl, isopropyl, n-butyl, isobutyl, tertiobutyl, sec-butyl, pentyl, neopentyl, n-hexyl, or cyclohexyl.

The term "cycloalkyl" designates an alkyl group as defined above and forms at least one cycle (e.g. cycloalkyl groups having 3 to 8 carbon atoms: cyclopropyl, cyclobutyl, cyclopentyl, cyclohexyl, cycloheptyl, and cyclooctyl).

The term "alkyloxy" refers to an alkyl chain linked to the molecule by means of an oxygen atom (an ether bond). The alkyl chain corresponds to the previously expressed definition. Methoxy, trifluoromethoxy, ethoxy, n-propyloxy, isopropyloxy, n-butoxy, iso-butoxy, tertio-butoxy, sec-butoxy, or hexyloxy can be given as examples.

The term "aryl" refers to aromatic groups comprising preferably from 5 to 14 carbon atoms, advantageously 6 to 14 carbon atoms, possibly interrupted by one or several heteroatoms selected among N, O, S or P (more specifically call "heteroaryl"). They are generally mono- or bi-cyclical and comprise advantageously from 6 to 14 carbon atoms, such as phenyl, α-naphtyl, β-naphtyl, anthracenyl or fluorenyl.

The term "oxygenated or sulfured heterocycle" designates a cycloalkyl group as defined above interrupted by one or several heteroatoms chosen among O and S. Thiopyran or pyran can be cited as examples.

By halogen atom, an atom of bromine, chlorine, fluorine or iodine is understood.

A halogenated alkyl radical is an alkyl radical as defined above which comprises at least one halogen atom or totally halogenated (perhalogenated).

Accordingly, the compounds of general formula (I) which present at least one of groups X3, X4 or X5 corresponding to a R3, G3R3, R4, G4R4, R5 or G5R5 formula, in which:
G3, G4, and G5 are as previously described, and
R3, R4, and R5, identical or different, represents an alkyl group substituted by one or several group 1 or group 2 substituent(s),
have therefore at least one of the groups R3, R4 and R5 of X3, X4 or X5 respectively representing an alkyl group substituted by one or several group 1 or group 2 substituent(s).

One particular aspect of the invention concerns compounds of general formula (I) in which A represents a carbonyl group (CO).

Another particular aspect of the invention concerns compounds of general formula (I) in which A represents an oxime group (C=N—O—H) or oxime ether (C=N—O—R8), R8 representing an alkyl group substituted or not by an aryl or cycloalkyl group. Preferably, R8 represents a methyl group.

Another particular aspect of the invention concerns compounds of general formula (I) in which A represents a —CR6R7 group, R6 representing a hydrogen atom and R7 representing a hydroxyl group, alkyl group, or a —OR8 group, R8 representing an alkyl group, substituted or not by an aryl or cycloalkyl group.

Preferably, the invention concerns compounds of general formula (I) in which A represents a —CR6R7 group, R6 representing a hydrogen atom and R7 represents a hydroxyl group.

Another preferred aspect of the invention concerns compounds of general formula (I) in which A represents a —CR6R7 group, R6 representing a hydrogen atom and R7 represents a —OR8 group, R8 being such as defined above. In particular, R8 represents an alkyl group comprising preferentially 1, 2, 3 or 4 carbon atoms. Even more preferably, R8 represents an alkyl group substituted by an aryl or cycloalkyl group, said aryl or cycloalkyl group comprising particularly 6 carbon atoms.

Another particular aspect of the invention concerns compounds of general formula (I) in which A represents a —CR6R7 group, in which R6 represents an alkyl group, or a —OR8 group and R7 represents a hydroxy group, an alkyl group, or a —OR8 group, R8 represents an alkyl group substituted or not by an aryl or cycloalkyl group.

Another particular subject-matter of the invention concerns compounds of general formula (I) in which X3 and X5, identical or different, represent respectively a R3 and R5 group, specifically with R3 and R5 representing a hydrogen atom.

Another particular subject-matter of the invention concerns compounds of general formula (I) in which X3 and X5, identical or different, represent respectively a R3 and R5 group, R3 and R5, identical or different, representing an alkyl group substituted or not by one or several group 1 or group 2 substituent(s), as previously defined.

Preferably, X3 and X5, identical or different, represent respectively a R3 and R5 group, R3 and R5, identical or different, representing a non-substituted alkyl group, comprising preferably 1, 2, 3 or 4 carbon atoms. Even more preferably, X3 and X5, identical or different, represent a methyl group.

Another particular aspect of the invention concerns compounds of general formula (I) in which X3 and X5, identical or different, represent respectively a G3R3 or G5R5 group, G3 and G5 being such as previously described, and R3 and R5 representing a hydrogen atom.

Another particular aspect of the invention concerns compounds of general formula (I) in which X3 and X5, identical or different, represent respectively a G3R3 or G5R5 group, G3 and G5 being such as previously described, and R3 and R5, identical or different, representing an alkyl group substituted or not by one or several group 1 or group 2 substituents, as previously defined.

Another particular aspect of the invention concerns compounds of general formula (I) in which X3 and X5, identical or different, represent respectively a G3R3 or G5R5 group, G3 and G5 being such as previously described, and R3 and R5, identical or different, representing an alkyl group substituted by one or several group 1 or group 2 substituents, as previously defined.

Another particular aspect of the invention concerns compounds of general formula (I) in which X4 represents a halogen atom (bromine, chlorine, fluorine, iodine).

Another particular aspect of the invention concerns compounds of general formula (I) in which X4 represents a R4 or G4-R4 group,
G4 being such as previously defined, and
R4 representing a hydrogen atom.

Another particular aspect of the invention concerns compounds of general formula (I) in which X4 represents a R4 or G4-R4 group,
G4 being such as previously defined, and
R4 representing an alkyl group substituted or not by one or several group 1 or group 2 substituents, as previously defined.

Another particular aspect of the invention concerns compounds general formula (I) in which X4 represents a R4 or G4-R4 group,
G4 being such as previously defined, and
R4 representing an alkyl group substituted by one or several group 1 or group 2 substituents(s). Preferably, G4 represents an oxygen atom and/or R4 represents an alkyl group substituted by a group 1 substituent, in particular COOH. Even more preferably, X4 represents a —OC(CH₃)₂COOH, —OCH₂COOH or —SC(CH₃)₂COOH group.

Another particular subject-matter of the invention concerns compounds of general formula (I) in which only one of the X3, X4 and X5 groups represents a R3, R4, R5, G3R3, G4R4 or G5R5 group,
G3, G4, and G5 being such as previously described, and
R3, R4, and R5, identical or different, representing an alkyl group substituted by one or several group 1 or group 2 substituent(s), as previously defined.

Another particular subject-matter of the invention concerns compounds of general formula (I) in which only X4 of the X3, X4, and X5 groups represents a R4 or G4R4,
G4 being such as previously defined, and
R4 representing an alkyl group substituted by one or several group 1 or group 2 substituents, as previously defined.

Another particular subject-matter of the invention concerns compounds of general formula (I) in which two or three of the X3, X4 and X5 groups represent a R3, R4, R5, G3R3, G4R4 or G5R5 group,
G3, G4, and G5 being such as previously described, and
R3, R4, and R5, identical or different, representing an alkyl group substituted by one or several group 1 or group 2 substituent(s), as previously defined.

Another particular aspect of the invention concerns compounds of general formula (I) in which G3, G4 and/or G5 represent(s) an oxygen atom.

Preferentially, the invention concerns compounds of general formula (I) in which only one of the X3, X4, or X5 groups corresponds to a G3R3, G4R4 or G5R5 formula,
G3, G4, and G5 representing an oxygen atom, and
R3, R4 or R5, identical or different, representing an alkyl group substituted by one or several group 1 or group 2 substituent(s), as previously defined.

Even more preferentially, the invention concerns compounds of general formula (I) in which only X4, among X3, X4, and X5, corresponds to the G4R4 formula,
G4 representing a hydrogen atom, and
R4 representing an alkyl group substituted by one or several group 1 or group 2 substituents, as previously defined.

Another preferential aspect of the invention concerns compounds of general formula (I) in which two or three of the X3, X4, or X5 groups correspond to the G3R3, G4R4 or G5R5 formula,
G3, G4, and G5 representing an oxygen atom, and
R3, R4, and R5 representing an alkyl group substituted by one or several group 1 or group 2 substituent(s), as previously defined.

A particular aspect of the invention concerns compounds of general formula (I) in which the substituent is chosen from among group 1 substituents. Preferentially, the group 1 substituent is a —COOR9 type, R9 being such as previously defined and representing preferably a hydrogen atom or an alkyl group comprising 1, 2, 3, 4, 5 or 6 carbon atoms.

A particular aspect of the invention concerns compounds general formula (I) in which only one of the X3, X4 or X5 groups corresponds to the formula —OC(CH₃)₂COOR9, R9 being such as previously defined and representing preferentially a hydrogen atom or an alkyl group comprising 1, 2, 3, 4, 5 or 6 carbon atoms.

Even more preferentially, X4 represents a —OC(CH₃)₂COOR9 group, R9 as previously defined and representing preferentially a hydrogen atom or an alkyl group comprising 1, 2, 3, 4, 5 or 6 carbon atoms.

One particular aspect of the invention concerns compounds of general formula (I) in which X1 represents a R1 or G1R1 carbonyl group,
G1 being such as previously defined, and
R1 representing a halogenated alkyl group.

Preferentially, R1 represents a halogenated alkyl group comprising 1, 2 or 3 carbon atoms.

Even more preferentially, X1 represents a —$CF_3$, —$OCF_3$, —$SCF_3$, —$ORCF_3$ group, R representing an alkyl group as defined above.

A particular aspect of the invention concerns compounds of general formula (I) in which X1 represents a halogen atom (bromine, chlorine, fluorine, iodine). Preferably, X1 represents an atom of chlorine or bromine.

A particular aspect of the invention concerns compounds of general formula (I) in which X2 represents a hydrogen atom.

A particular aspect of the invention concerns compounds of general formula (I) in which X2 represents a halogen atom (bromine, chlorine, fluorine, iodine).

A particular subject-matter of the invention concerns compounds of general formula (I) in which X2 represents a R2 or G2R2 group, R2 and G2 being such as previously described. Preferentially, R2 represents a hydrogen atom, a —$CF_3$ group or an alkyl group comprising 1, 2, 3, 4, 5, 6, 7 or 8 carbon atoms. Even more preferentially, X2 represents a —OR' group, R' representing an alkyl group, —$CF_3$, —$OCF_3$, —OH.

A particular aspect of the invention concerns compounds of general formula (I) in which D represents a $CH_2$ group.

Another particular subject-matter of the invention concerns compounds of general formula (I) in which G2 and D form an oxygenated or sulfured heterocycle so as to form compounds having the following formula (II):

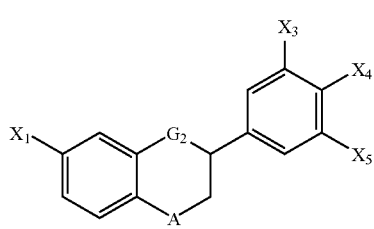

(II)

Preferably, G2 represents a sulfur atom in general formula (II).

In accordance with a particular embodiment of the invention, the preferred compounds are indicated below:

Compound 1: 2-[2,6-dimethyl-4-[3-[4-(trifluoromethyloxy)phenyl]-3-oxo-propyl]phenoxy]-2-methyl-propanoic acid Compound 2: 2-[2,6-dimethyl-4-[3-[4-(trifluoromethylthio)phenyl]-3-oxo-propyl]phenoxy]-2-methylpropanoic acid

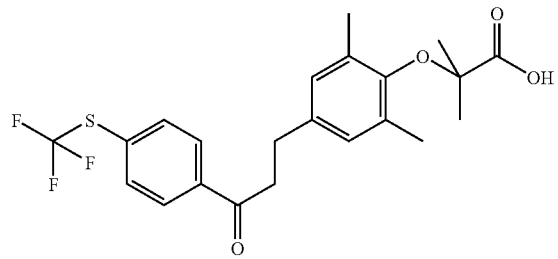

Compound 3: 2-[2,6-dimethyl-4-[3-[4-bromophenyl]-3-oxo-propyl]phenoxy]-2-methylpropanoic acid

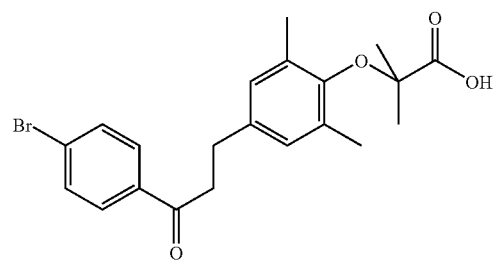

Compound 4: 2-[2,6-dimethyl-4-[3-[4-(trifluoromethyl)phenyl]-3-oxo-propyl]phenoxy]-2-methylpropanoic acid Compound 5: 2-[4-[3-[4-chloro-2-hydroxyphenyl]-3-oxo-propyl]phenylthio]-2-methylpropanoic acid

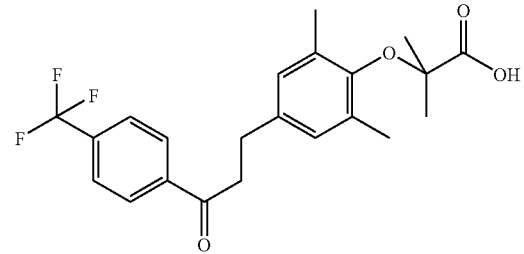

Compound 6: 2-[2-methyl-4-[3-[4-(3,3,3-trifluoropropyloxy)phenyl]-3-oxo-propyl]phenoxy]-2-methylpropanoic acid

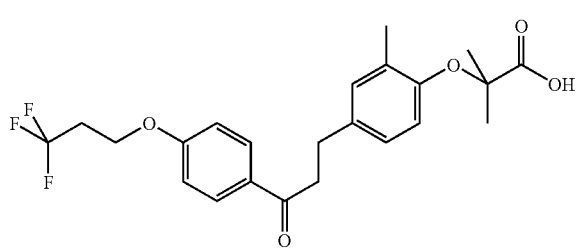

Compound 7: 2-[2,6-dimethyl-4-[3-hydroxy-3-[4-(trifluoromethylthio)phenyl]propyl]phenoxy]-2-methylpropanoic acid

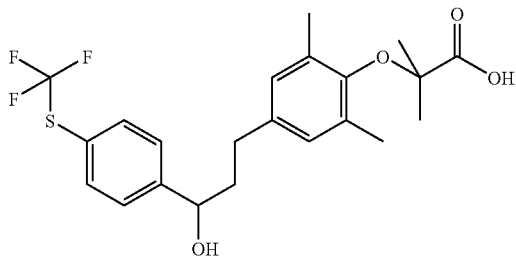

Compound 8: 2-[2,6-dimethyl-4-(3-(pyridin-3-ylmethoxy)-3-[4-(trifluoromethoxy)phenyl]propyl]phenoxy]-2-methylpropanoic acid

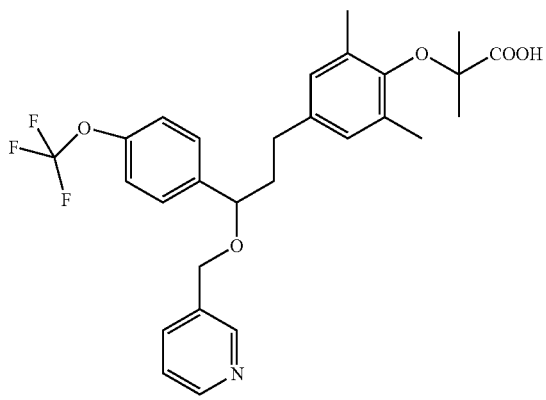

Compound 9: 2-[4-(3-(4-iodobenzyloxy)-3-(4-(trifluoromethoxy)phenyl)propyl)-2,6-dimethylphenoxy]-2-methylpropanoic acid

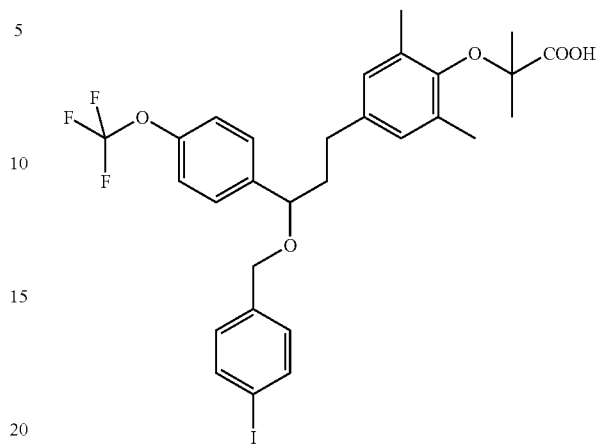

Compound 10: 2-[4-(3-methoxy-3-(4-(trifluoromethoxy)phenyl)propyl)-2,6-dimethylphenoxy]-2-methylpropanoic acid

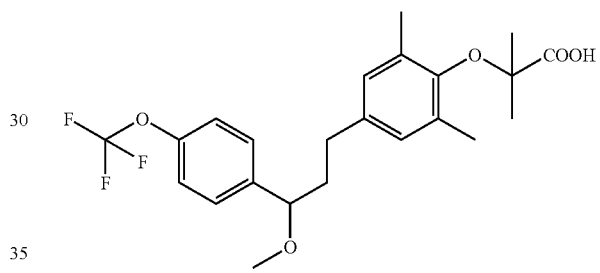

Compound 11: 2-[2,6-dimethyl-4-[3-[4-(3,3,3-trifluoropropyloxy)phenyl]-3-oxo-propyl]phenoxy]-2-methylpropanoic acid

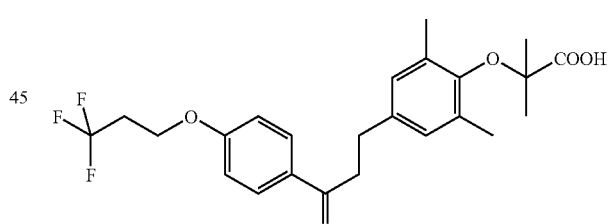

Compound 12: 2-(2,6-dimethyl-4-(3-oxo-3-(4-(2,2,2-trifluoroethoxy)phenyl)propyl)phenoxy)-2-methylpropanoic acid

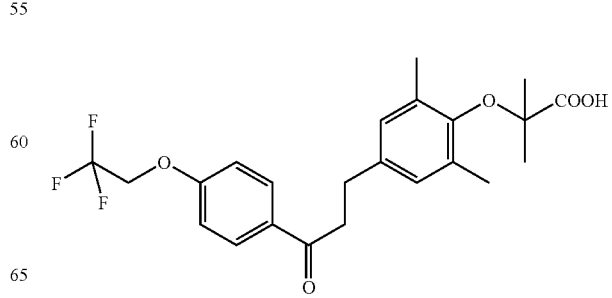

Compound 13: 2-(2,6-dimethyl-4-(3-oxo-3-(4-(2,2,2-trifluoroethylthio)phenyl)propyl)phenoxy)-2-methylpropanoic acid

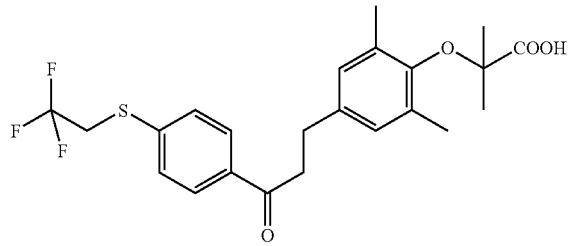

Compound 14: 2-(4-(3-(4-chloro-2-(methylthio)phenyl)-3-oxo-propyl)-2,6-dimethylphenoxy)-2-methylpropanoic acid

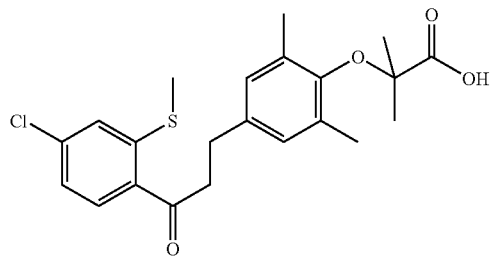

Compound 15: 2-(4-(3-(2,4-bis(trifluoromethyl)phenyl)-3-oxo-propyl)-2,6-dimethylphenoxy)-2-methylpropanoic acid

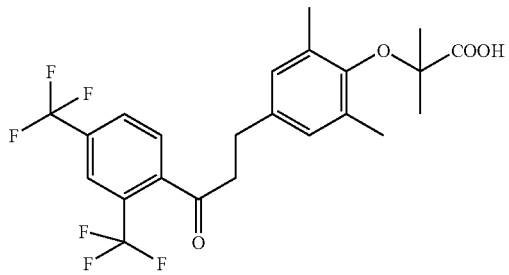

Compound 16: 2-(4-(3-(2-fluoro-4-(trifluoromethyl)phenyl)-3-oxo-propyl)-2,6-dimethylphenoxy)-2-methylpropanoic acid

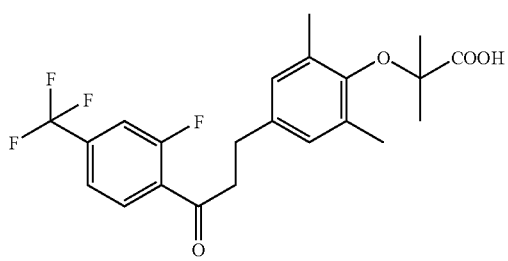

Compound 17: 2-(4-(3-(2-fluoro-4-(2,2,2-trifluoroethoxy)phenyl)-3-oxo-propyl)-2,6-dimethylphenoxy)-2-methylpropanoic acid

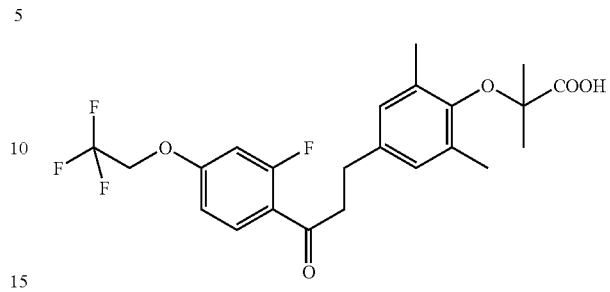

Compound 18: 2-(2,6-dimethyl-4-(3-(2-methyl-4-(2,2,2-trifluoroethoxy)phenyl)-3-oxo-propyl)phenoxy)-2-methylpropanoic acid

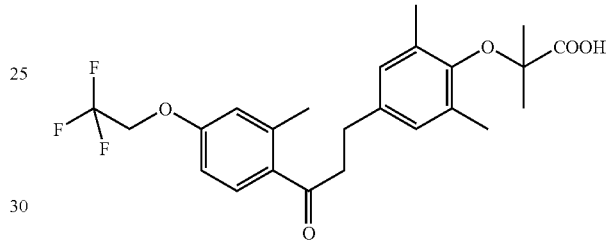

Compound 19: 2-(4-(3-(2-methoxy-4-(2,2,2-trifluoroethoxy)phenyl)-3-oxo-propyl)-2,6-dimethylphenoxy)-2-methylpropanoic acid

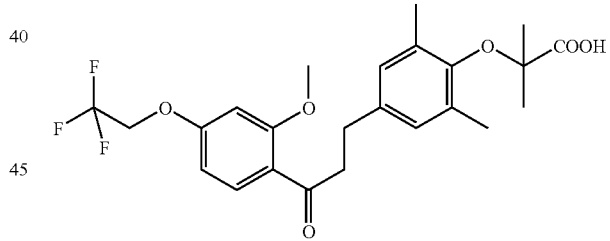

Compound 20: 2-(4-(3-(2-hydroxy-4-(trifluoromethyl)phenyl)-3-oxo-propyl)-2,6-dimethylphenoxy)-2-methylpropanoic acid

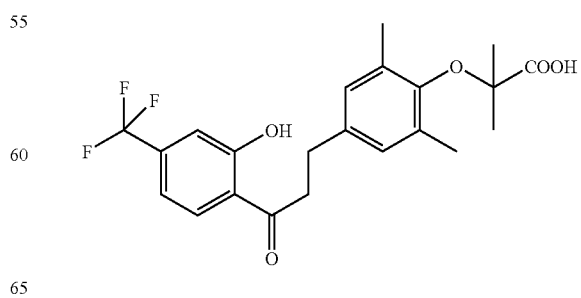

Compound 21: 2-(4-(3-(2-methoxy-4-(trifluoromethyl)phenyl)-3-oxo-propyl)-2,6-dimethylphenoxy)-2-methylpropanoic acid

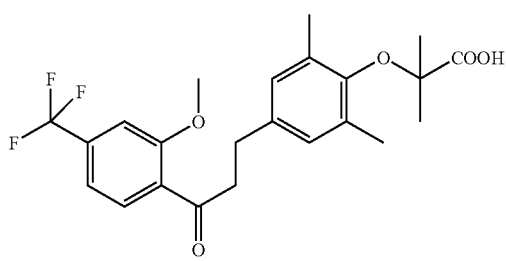

Compound 22: 2-(2,6-dimethyl-4-(3-(2-isopropyloxy-4-(trifluoromethyl)phenyl)-3-oxo-propyl)phenoxy)-2-methylpropanoic acid

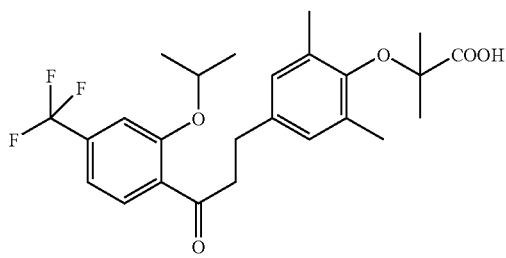

Compound 23: 2-(2,6-dimethoxy-4-(3-oxo-3-(4-(trifluoromethoxy)phenyl)propyl)phenoxy)-2-methylpropanoic acid

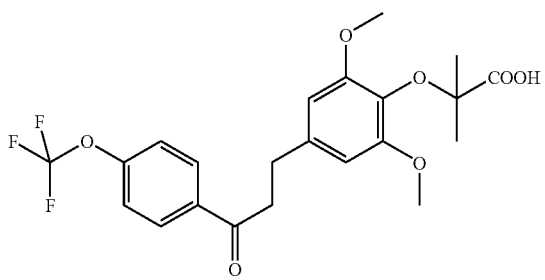

Compound 24: 2-(4-(3-(2-fluoro-4-(trifluoromethyl)phenyl)-3-oxo-propyl)-2,6-dimethoxyphenoxy)-2-methylpropanoic acid

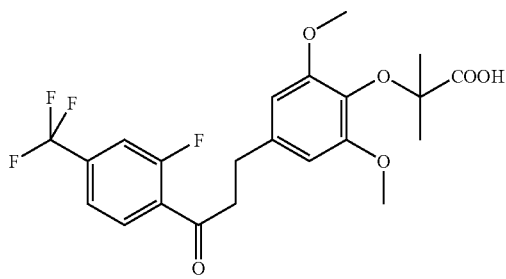

Compound 25: 2-methyl-2-(2-methyl-4-(3-oxo-3-(4-(trifluoromethylthio)phenyl)propyl)phenoxy)propanoic acid

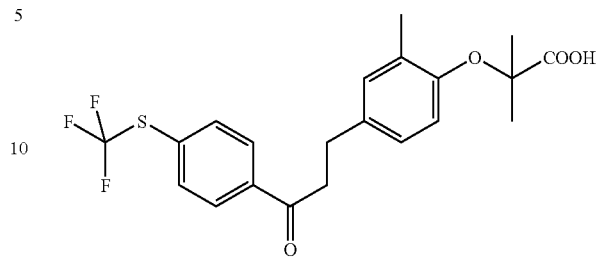

Compound 26: 2-methyl-2-(2-methyl-4-(3-oxo-3-(4-(trifluoromethoxy)phenyl)propyl)phenoxy)propanoic acid

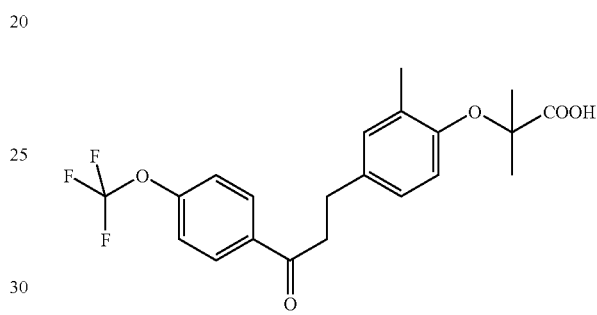

Compound 27: 2-(4-(3-(2-fluoro-4-(trifluoromethyl)phenyl)-3-oxo-propyl)phenylthio)-2-methylpropanoic acid

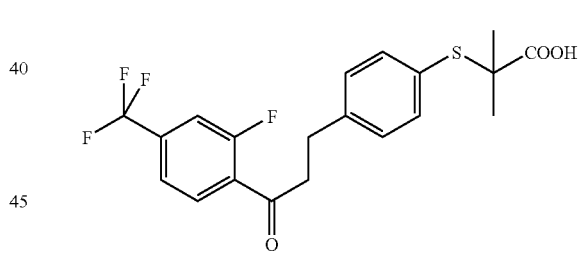

Compound 28: 2-methyl-2-(3-(3-oxo-3-(4-(trifluoromethoxy)phenyl)propyl)phenoxy)propanoic acid

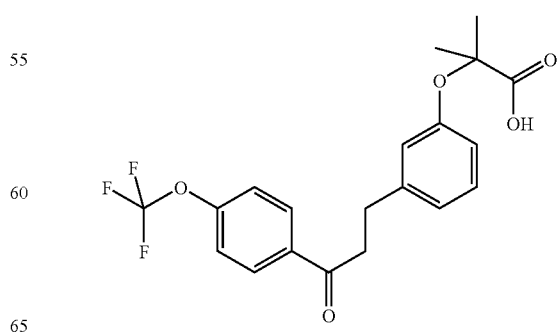

Compound 29: 2-(2,6-dimethyl-4-(3-oxo-3-(4-(trifluoromethoxy)phenyl)propyl)phenoxy)propanoic acid

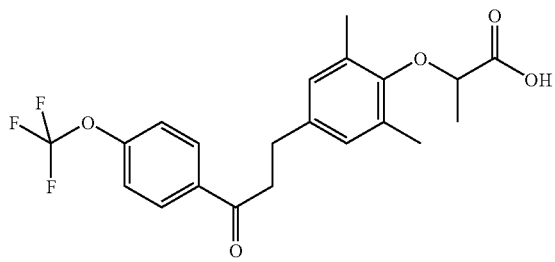

Compound 30: 2-[4-(3-hydroxy-3-(4-(trifluoromethoxy)phenyl)propyl)-2,6-dimethylphenoxy]-2-methylpropanoic acid

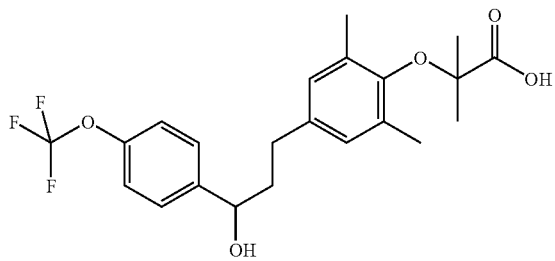

Compound 31: 2-(2,6-dimethyl-4-(3-oxo-3-(4-(trifluoromethoxy)phenyl)propyl)phenoxy)-2-methylpropanamide

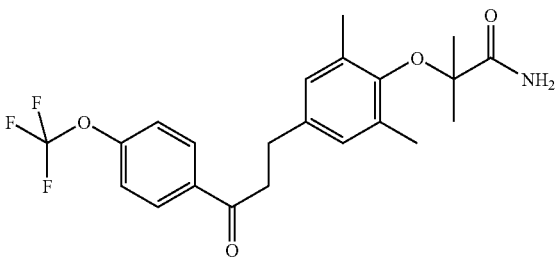

Compound 32: 2-(4-(3-hydroxyimino-3-(4-(trifluoromethoxy)phenyl)propyl)-2,6-dimethylphenoxy)-2-methylpropanoic acid

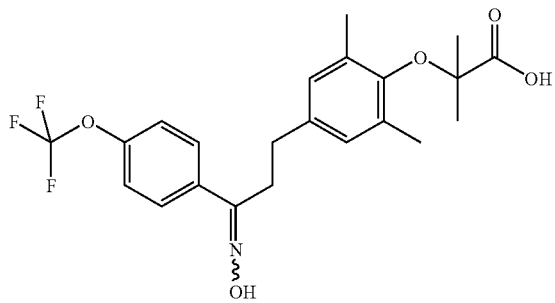

Compound 33: 2-(4-(3-methoxyimino-3-(4-(trifluoromethoxy)phenyl)propyl)-2,6-dimethylphenoxy)-2-methylpropanoic acid

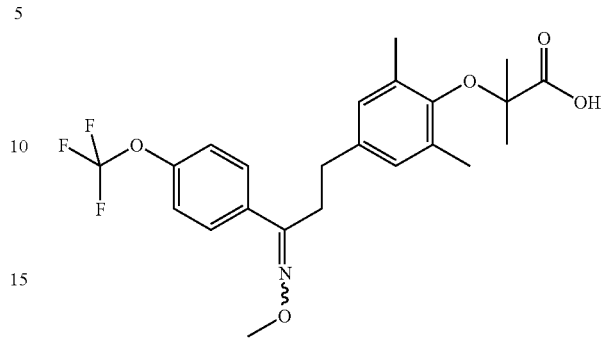

Compound 34: 4-(2,6-dimethyl-4-(3-oxo-3-(4-(trifluoromethoxy)phenyl)propyl)phenoxy)-2,2-dimethylbutanoic acid

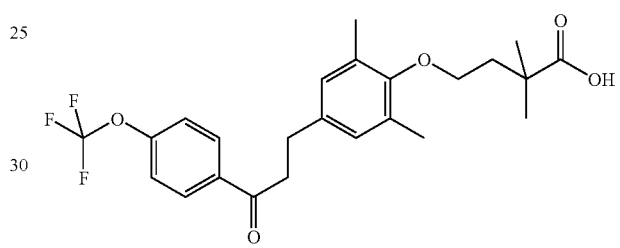

Compound 35: 2-(2,6-dimethyl-4-(3-oxo-3-(4-(trifluoromethoxy)phenyl)propyl)phenoxy)-2-methylpropanoic acid tertiobutyl ester

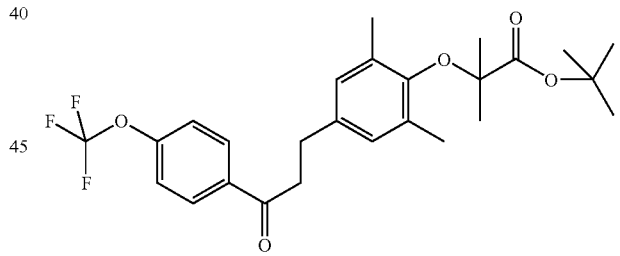

Compound 36: 2-(2,6-dimethyl-4-(3-oxo-3-(4-(trifluoromethoxy)phenyl)propyl)phenoxy)-2-methylpropanoic isopropyl ester

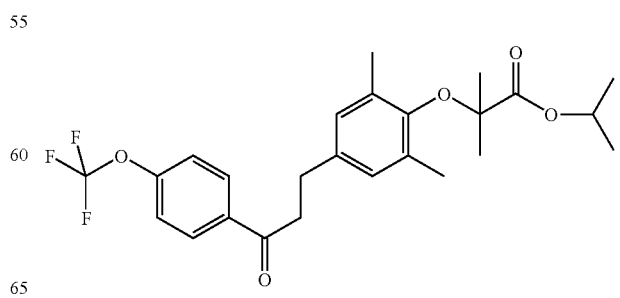

Compound 37: 2,2-difluoro-2-(2,6-dimethyl-4-(3-oxo-3-(4-(trifluoromethoxy)phenyl)propyl)phenoxy)acetic acid

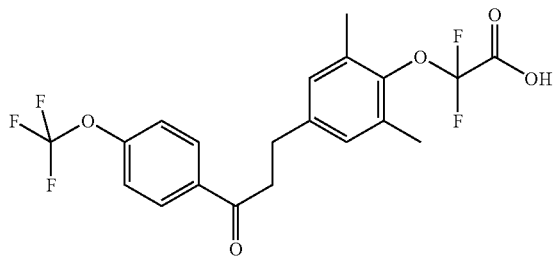

Compound 38: 2-(2-methoxy-4-(3-oxo-3-(4-(trifluoromethoxy)phenyl)propyl)phenylthio)-2-methylpropanoic acid

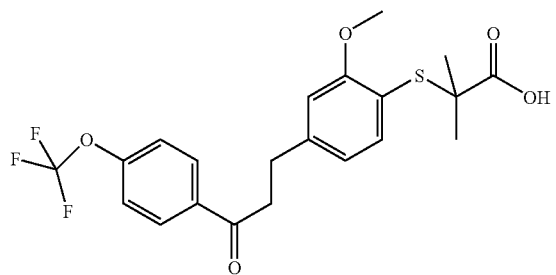

The invention concerns more preferentially the following compounds:
Compound 1: 2-[2,6-dimethyl-4-[3-[4-(trifluoromethoxy)phenyl]-3-oxo-propyl]phenoxy]-2-methylpropanoic acid;
Compound 2: 2-[2,6-dimethyl-4-[3-[4-(trifluoromethylthio)phenyl]-3-oxo-propyl]phenoxy]-2-methylpropanoic acid;
Compound 3: 2-[2,6-dimethyl-4-[3-[4-bromophenyl]-3-oxo-propyl]phenoxy]-2-methylpropanoic acid;
Compound 4: 2-[2,6-dimethyl-4-[3-[4-(trifluoromethyl)phenyl]-3-oxo-propyl]phenoxy]-2-methylpropanoic acid
Compound 6: 2-[2-methyl-4-[3-[4-(3,3,3-trifluoropropyloxy)phenyl]-3-oxo-propyl]phenoxy]-2-methylpropanoic acid
Compound 11: 2-[2,6-dimethyl-4-[3-[4-(3,3,3-trifluoropropyloxy)phenyl]-3-oxo-propyl]phenoxy]-2-methylpropanoic acid
Compound 26: 2-methyl-2-(2-methyl-4-(3-oxo-3-(4-(trifluoromethoxy)phenyl)propyl)phenoxy)propanoic acid
Compound 36: 2-(2,6-dimethyl-4-(3-oxo-3-(4-(trifluoromethoxy)phenyl)propyl)phenoxy)-2-methylpropanoic acid isopropyl ester The compounds of the present invention include their stereoisomers (diastereoisomers, enantiomers), pure or mixed, racemic forms, their geometric isomers, their tautomers, their salts, their hydrates, their solvates, their solid forms, and mixtures thereof.

The compounds according to the invention can comprise one or several asymmetrical centers. The present invention includes stereoisomers (diastereoisomers, enantiomers), pure or mixed, as well as racemic forms and geometrical isomers. When an enantiomerically pure (or enriched) mixture is desired, it can be obtained either by purification of the final product or chiral intermediates, or by asymmetrical synthesis following the methods known by one of ordinary skill in the art (for example, using reagents and chiral catalysts). Some compounds according to the invention can have different stable tautomeric forms and all these forms as well as their mixtures are included in the invention.

This invention also concerns "pharmaceutically acceptable" salts of compounds according to the invention. Generally, this term designates slightly- or non-toxic salts obtained from organic or inorganic bases or acids. These salts may be obtained during the final purification step of the compound according to the invention or by incorporating the salt into the purified compound.

Some compounds according to the invention and their salts could be stable in several solid forms. The present invention includes all the solid forms of the compounds according to the invention which includes amorphous, polymorphous, mono- and polycrystalline forms.

The compounds according to the invention can exist in non-solvated or solvated form, for example with pharmaceutically acceptable solvents such as water (hydrates) or ethanol.

Compounds according to the invention labeled with one or more isotopes are also included in the invention: these compounds are structurally identical but different by the fact that at least one atom of the structure is replaced by an isotope (radioactive or not). Examples of isotopes that can be included in the structure of the compounds according to the invention can be chosen among hydrogen, carbon, oxygen, and sulfur such as $^2H$, $^3H$, $^{13}C$, $^{14}C$, $^{18}O$, $^{17}O$, $^{35}S$ respectively. Radioactive isotopes are particularly preferable since they are easy to prepare and detect within the scope of in vivo bioavailability studies of the substances. Heavy isotopes (such as $^2H$) are particularly preferred because of their use as internal standards in analytical studies.

The present invention also concerns a process of synthesis of compounds of general formula (I) as previously defined.

The process of the present invention comprises:
a step of mix (i) in a basic or acidic medium of at least one compound of formula (A) with at least one compound of formula (B):

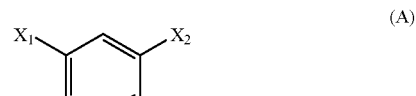
(A)

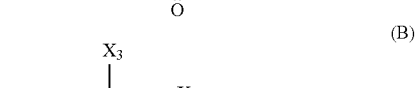
(B)

In which X1, X2, X3, X4, and X5 have the previously given definitions,
then (ii) a reduction step of the resulting compounds,
and eventually (iii) a step allowing the linking of functional groups.

The experimental conditions for step (i) in an acidic or basic medium and for step (ii) are easy to implement for the person skilled in the art and may vary greatly. The procedures of the syntheses can be particularly those described under "examples" in this invention.

The mix of the two compounds is advantageously performed stoichiometrically. This is performed preferably at room temperature (between about 18° C. and 25° C.) and at normal atmospheric pressure.

In a basic medium, the reaction takes place preferably in the presence of a strong base, such as an alkali metal hydroxide, like sodium hydroxide or an alkali metal alcoholate like sodium ethylate.

In an acidic medium, the reaction takes place preferably in the presence of a strong acid, such as hydrochloric acid.

The resulting compounds can be isolated by classic methods of one of ordinary skill in the art. They could then be used, for example, as medicines or cosmetic products.

The present invention is also directed to compounds such as above described as medicines.

Another subject-matter of the present invention concerns a pharmaceutical composition comprising, in a pharmaceutically acceptable support, at least one compound as above described, possibly in association with one or several other therapeutic and/or cosmetic active constituents.

It preferably concerns a pharmaceutical composition for the treatment of complications associated with metabolic syndrome, insulin resistance, diabetes, dyslipidemias, atherosclerosis, cardiovascular diseases, obesity, hypertension, inflammatory diseases (asthma, etc.), neurodegenerative pathologies (Alzheimer's disease, etc.), or cancer, etc. The pharmaceutical composition according to the invention is preferably used for treating dyslipidemias.

It is preferably a pharmaceutical composition for treating cardiovascular risk factors related to a deregulation of lipid and/or glucid metabolism disorders (hyperlipidemia, type II diabetes, obesity, etc.) by reducing the global risk.

Another subject-matter of the invention concerns a nutritional composition including at least one compound as above described.

Another subject-matter of the invention concerns the use of at least one compound as previously described for the preparation of pharmaceutical compositions intended for treating multiple pathologies, particularly the ones related to metabolism disorders (e.g. dyslipidemias). More generally, the subject-matter of the invention concerns the use of at least one compound previously described for the preparation of pharmaceutical compositions intended for treating the cardiovascular disease risk factors related to lipid and/or glucid metabolism disorders, in order to reduce the global risk.

For example (but not limitatively), the compounds according to the invention ideally may be advantageously administered in combination with other therapeutic and/or cosmetic agents, currently available in the market or in development, such as:

anti-diabetics: secretagogues (sulfonylurea (glibenclamide, glimepiride, gliclazide, etc.) and glinides (repaglinide, nateglinide, etc.)), alpha-glucosidase inhibitors, PPARγ agonists (thiazolidinediones such as rosiglitazone, pioglitazone), mixed PPARα/γ agonists (tesaglitazar, muraglitazar), pan-PPARs (compounds that simultaneously activate the 3 PPAR isoforms), biguanides (metformin), Dipeptidyl Peptidase IV inhibitors (MK-431, vildagliptin), Glucagon-Like Peptide-1 (GLP-1) agonists (exenatide), etc.

insulin ipid-lowering and/or cholesterol-lowering molecules: fibrates (fenofibrate, gemfibrozil), HMG CoA reductase inhibitors or hydroxylmethylglutaryl coenzyme A reductase (statins such as atorvastatin, simvastatin, fluvastatin), cholesterol absorption inhibitors (ezetimibe, phytosterols), CETP or cholesteryl ester transfer protein inhibitors (torcetrapib), ACAT or acyl-coenzyme a cholesterol acyltransferase (avasimibe, eflucimibe), MTP (Microsomal Triglyceride Transfer Protein) inhibitors, biliary acid sequestering agents (cholestyramine), vitamin E, polyunsaturated fatty acids, omega-3 fatty acids, nicotinic acid type derivatives (niacin), etc.

anti-hypertensive agents and hypotensive agents: ACE (Angiotensin-Converting Enzyme) inhibitors (captopril, enalapril, ramipril, or quinapril), angiotensin II receptor antagonists (losartan, valsartan, telmisartan, eposartan, irbesartan, etc.), beta blockers (atenolol, metoprolol, labetalol, propranolol), thiazide and non-thiazide diuretics (furosemide, indapamide, hydrochlorthiazide, anti-aldosterone), vasodilators, calcium channel blockers (nifedipine, felodipine, or amlodipine, diltiazem or verapamil), etc.

anti-platelet agents: Aspirin, Ticlopidine, Dipyridamole, Clopidogrel, Flurbiprofen, etc.

anti-obesity agents: Sibutramine, lipase inhibitors (orlistat), PPARδ, cannabinoid CB1 receptor antagonists (rimonabant), etc.

anti-inflammatory agents: for example, corticoids (prednisone, betamethasone, dexamethasone, prednisolone, methylprednisolone, hydrocortisone, etc.), NSAIDs or non-steroidal anti-inflammatory drugs derived from indole (indomethacin, sulindac), NSAIDs of the arylcarboxylic group (tiaprofenic acid, diclofenac, etodolac, flurbiprofen, ibuprofen, ketoprofen, naproxen, nabumetone, alminoprofen), NSAIDs derived from oxicam (meloxicam, piroxicam, tenoxicam), NSAIDs from the fenamate group, COX2 selective inhibitors (celecoxib, rofecoxib), etc.

antioxidant agents: for example probucol, etc.

agents used in the treatment of cardiac insufficiency: thiazidic and non-thiazidic diuretics (furosemide, indapamide, hydrochlorthiazide, antialdosterone), ACE inhibitors (captopril, enalapril, ramipril or quinapril), digitalis drugs (digoxin, digitoxin), beta blockers (atenolol, metoprolol, labetalol, propranolol), phosphodiesterase inhibitors (enoximone, milrinone), etc.

agents used in the treatment of coronary insufficiency: beta blockers (atenolol, metoprolol, labetalol, propranolol), calcium channel blockers (nifedipine, felodipine, or amlodipine, bepridil, diltiazem or verapamil), NO (nitric oxide) donors (trinitrine, isosorbide dinitrate, molsidomine), amiodarone, etc.

anti-cancer drugs: cytotoxic agents (agents interacting with DNA (Deoxyribonucleic Acid), alkylating agents, cisplatin, and derivatives), cytostatic agents (GnRH (Gonatropin-Releasing Hormone) analogues, somatostatin analogues, progestin, anti-oestrogen drugs, aromatase inhibitors, etc.), immune response modulators (interferons, IL2, etc.), etc.

antiasthmatic drugs such as bronchodilators (beta 2 receptor agonists), corticoids, cromoglycate, leucotriene receptor antagonists (montelukast), etc.

corticoids used in the treatment of skin pathologies such as psoriasis and dermatitis vasodilators and/or anti-ischemic agents (buflomedil, ginkgo biloba extract, naftidrofuryl, pentoxifylline, piribedil), etc.

The invention also concerns a method for treating pathologies related to lipid and/or glucid metabolism comprising the administration to a subject, in particular a human, of an effective quantity of a compound or a pharmaceutical composition as above-defined. Within the context of the invention, the term "an effective quantity" refers to an amount of the compound sufficient to produce the desired biological result. Within the context of the invention, the term "subject" means a mammal and more particularly a human.

The term "treatment" designates curative, symptomatic, or preventative treatment. The compounds of this invention can thus be used upon subjects (such as mammals, in particular humans) having a declared disease. The compounds of this invention can also be used to delay or slow down the progress or prevent the further progress of the disease, thus improving the subjects' condition. The compounds of this invention can finally be administered to healthy subjects that might normally develop the disease or have a significant risk of developing the disease.

Pharmaceutical compositions according to the invention advantageously comprise one or several excipients or vehicles, acceptable within a pharmaceutical context (e.g. saline solutions, physiological solutions, isotonic solutions, etc., compatible with pharmaceutical usage and well-known by one of ordinary skill in the art). The compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. The compositions can be formulated in the form of injectable suspensions, gels, oils, pills, suppositories, powders, gelcaps, capsules, aerosols, etc., eventually by means of galenic forms or devices assuring a prolonged and/or slow release. For this kind of formulation, agents such as cellulose, carbonates or starches can advantageously be used.

The compounds or compositions according to the invention can be administered in different ways and in different forms. Thus, for example, they can be administered in a systematic way, per os, parenterally, by inhalation, or by injection, such as for example intravenously, by intramuscular route, by subcutaneous route, by transdermal route, by intra-arterial route, etc. For the injections, the compounds are generally conditioned in the form of liquid suspensions which can be injected using syringes or perfusions, for example.

It is understood that the speed and/or the dose relative to the injection can be adapted by one of ordinary skill in the art, in function of the patient, the pathology, the form of administration, etc. Typically, the compounds are administered at doses varying between 1 μg and 2 g per administration, preferentially from 0.1 mg to 1 g per administration. Administration can be daily or even several times per day, if necessary. Additionally, the compositions according to the invention can include other agents or active constituents.

LEGENDS TO THE FIGURES

Abbreviation Used in These Figures:
 Cpd=compound
 Ctrl=control
 mpk=mg/kg/day
 LDL-cholesterol=Low Density Lipoprotein cholesterol
 HDL-cholesterol=High Density Lipoprotein cholesterol
 VLDL-cholesterol=Very Low Density Lipoprotein cholesterol
 FIGS. 1-1 to 1-18: In Vitro Evaluation of the PPAR-Activating Properties of the Compounds of the Invention According to the Dose The activation of PPARs is evaluated in vitro using a monkey kidney fibroblast line (COS-7), by measuring the transcriptional activity of chimeras made up of the DNA binding domain of the Gal4 transcription factor of yeast and of the binding domain to the ligand of the different PPARs.

Figures 1, 2:
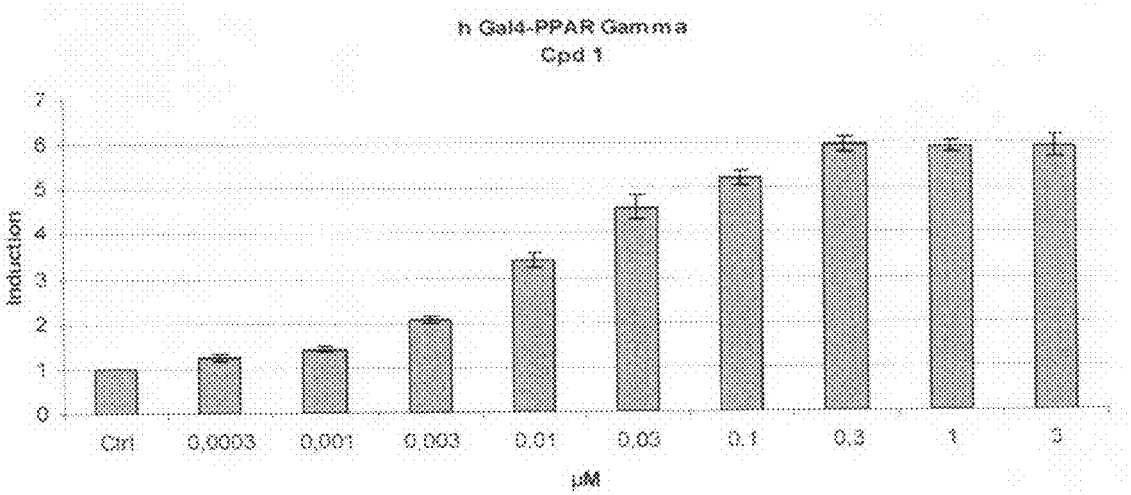
Figures 1, 2, 3:
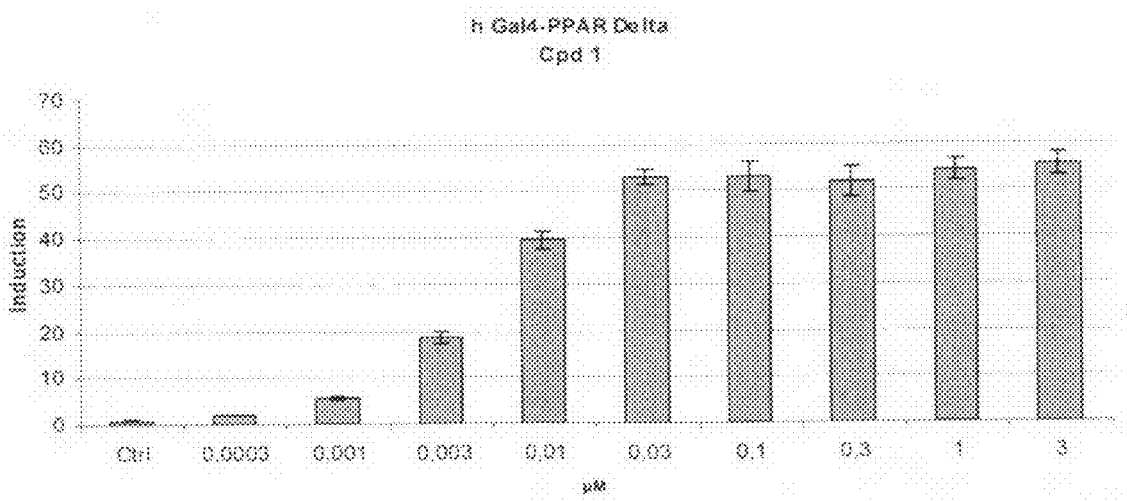

The compounds are tested in doses of between $10^{-7}$ and 100 μM on Gal4-PPARα, γ, and δ chimeras. The induction factor, i.e. the ratio between the luminescence induced by the compound and the luminescence induced by the control, is measured for each condition. The higher the induction factor is, the more the compound has PPAR activating properties.
 FIGS. 1-1, 1-2, 1-3: In vitro evaluation of the PPARα, γ, δ activating properties of compound 1
 FIGS. 1-4, 1-5, 1-6: In vitro evaluation of the PPARα, γ, δ activating properties of compound 2
 FIGS. 1-7, 1-8, 1-9: In vitro evaluation of the PPARα, γ, δ activating properties of compound 3
 FIGS. 1-10, 1-11, 1-12: In vitro evaluation of the PPARα, γ, δ activating properties of compound 4
 FIGS. 1-13, 1-14, 1-15: In vitro evaluation of the PPARα, γ, δ activating properties of compound 5
 FIGS. 1-16, 1-17, 1-18: In vitro evaluation of the PPARα, γ, δ activating properties of compound 7
 FIGS. 2-1 to 2-7: In Vivo Evaluation, on ApoE2/E2 Mice, of Body-Weight Properties, of Hypolipidemic Properties, and Properties Stimulating the Synthesis of HDL-Cholesterol of the Compounds According to the Invention The effect of the compounds according to the invention is evaluated in vivo on mice humanized by the E2 isoform apolipoprotein E (E2/E2).

The dyslipidemic E2/E2 mouse's body weight, rates of total cholesterol, triglycerides and of plasma free fatty acids are measured after 8 days of a per os treatment with the compounds according to the invention. These parameters are compared to those obtained from the control animals (animal not treated with the compounds according to the invention): the measured difference shows the effect on body weight and the hypolipidemic effect of the compounds according to the invention
 FIG. 2-1: Body weight gain after 8 days of treatment with compound 1, administered at 5, 10, and 50 mpk
 FIG. 2-2: Plasma cholesterol levels after 8 days of treatment with compound 1, administered at 5, 10, and 50 mpk;
 FIG. 2-3: Plasma HDL cholesterol levels after 8 days of treatment with compound 1, administered at 5, 10, and 50 mpk
 FIG. 2-4: Plasma triglyceride levels after 8 days of treatment with compound 1, administered at 5, 10, and 50 mpk.
 FIG. 2-5: Plasma free fatty acid levels after 8 days of treatment with compound 1, administered at 5, 10, and 50 mpk.

The effectiveness of the compounds according to the invention is also evaluated by measuring, in the hepatic tissue, the expression of genes involved in lipid and/or glucid metabolism and in energy dissipation. Each level of gene expression is normalized regarding the expression level of the reference gene 36B4. The induction factor, i.e. the ratio between the relative signal (induced by the compound according to the invention) and the average of the relative values obtained with the control group, is then calculated. The higher the induction factor is, the more the compound promotes hepatic gene expression. The final result is represented as the average of the induction values obtained with each experimental group.
 FIG. 2-6: Expression of PDK4 (Pyruvate Dehydrogenase Kinase, isoform 4) in the hepatic tissue of the E2/E2 mouse, after 8 days of treatment with compound 1, administered at 5, 10, and 50 mpk FIG. 2-7: Expression of ApoCIII (Apolipoprotein C3) in the hepatic tissue of the E2/E2 mouse, after 8 days of treatment with compound 1, administered at 5, 10, and 50 mpk FIGS. 3-1 to 3-5: In Vivo Evaluation, on the C57BI6 Mouse, of Body-Weight Properties, of Hypolipidemic Properties, and Properties Stimulating the Synthesis of HDL-Cholesterol of the Compounds According to the Invention The effect of the compounds according to the invention is evaluated in vivo on the C57BI6 mouse by measuring the body weight evolution, the plasma HDL cholesterol and triglyceride levels, after 14 days of a per os treatment with the compounds according to the invention. These parameters are compared to those obtained with the control animals (animals not treated with the compounds according to the invention): the measured difference shows the effect the compounds according to the invention have on the body weight, and shows their hypolipidemic effect.

FIG. 3-1: Body weight gain after 14 days of treatment with compound 1, administered at 3, 10, and 30 mpk FIG. 3-2: Plasma HDL cholesterol levels after 14 days of treatment with compound 1, administrated at 3, 10, and 30 mpk FIG. 3-3: Plasma triglyceride levels after 14 days of treatment with compound 1, administered at 3, 10, and 30 mpk The effectiveness of the compounds according to the invention is also evaluated by measuring, in hepatic tissue, the expression of the genes involved in lipid metabolism. Each level of gene expression is normalized regarding the expression level of the reference gene 36B4. The induction factor is then calculated. The higher the induction factor is, the more the compound promotes hepatic gene expression. The final result is represented as the average of the induction values obtained with each experimental group.

Figures 1, 2, 3, 4:
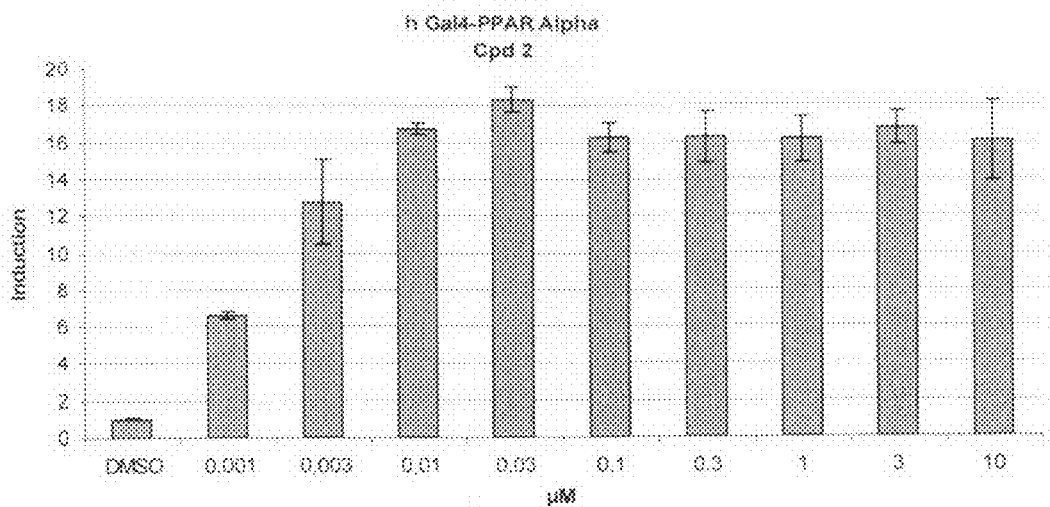

FIG. 3-4: Expression of PDK4 in the hepatic tissue of the C57BI6 mouse, after 14 days of treatment with compound 1, administered at 3, 10, and 30 mpk FIG. 3-5: Expression of ApoCIII in the hepatic tissue of the C57BI6 mouse, after 14 days of treatment with compound 1, administered at 3, 10, and 30 mpk FIGS. 4-1 to 4-9: In Vivo Evaluation, on db/db Mouse, of Body-Weight Properties, of Antidiabetic Properties, Hypolipidemic Properties, and Properties stimulating the Synthesis of HDL-Cholesterol of the Compounds According to the Invention The effect of the compounds according to the invention is evaluated in vivo on the db/db mouse by measuring the body weight evolution, the glucose levels, the insulin levels, the plasma total cholesterol and triglyceride levels, and by analyzing the distribution of cholesterol in different plasma lipoprotein fractions, after 28 days of a per os treatment with compounds according to the invention. These parameters are compared to the ones obtained with the control animals (animals not treated with the compounds according to the invention): the measured difference shows the effects the compounds according to the invention have on the body weight, the insulin-resistance, and shows their hypolipidemic effect.

FIG. 4-1: Body weight gain after 28 days of treatment with compound 1, administrated at 50 mpk;

FIG. 4-2: Glycemia after 28 days of treatment with compound 1, administrated at 50 mpk FIG. 4-3: Insulemia after 28 days of treatment with compound 1, administrated at 50 mpk FIG. 4-4: Plasma cholesterol levels after 14 days of treatment with compound 1 and compound 3, administrated at 50 mpk FIG. 4-5: Distribution of cholesterol among different plasma lipoprotein fractions after 28 days of treatment with compound 1 and compound 3, administrated at 50 mpk FIG. 4-6: Plasma triglyceride levels after 28 days of treatment with compound 1 and compound 3, administrated at 50 mpk FIG. 4-7: Plasma free fatty acid levels after 28 days of treatment with compound 1 and compound 3, administered at 50 mpk.

The effectiveness of the compounds according to the invention is also evaluated by measuring, in the hepatic and muscular (skeletal) tissues, the expression of genes involved in lipid and/or glucid metabolism and in energy dissipation. Each level of gene expression is normalized regarding the expression level of the reference gene 36B4 in the hepatic tissue, or regarding the expression level of the reference gene 18S in the gastrocnemius skeletal muscle. The induction factor, i.e. the ratio between the relative signal (induced by the compound according to the invention) and the average of the relative values obtained with the control group, is then calculated. The higher the induction factor is, the more the greater the compound promotes gene expression. The final result is represented as the average of the induction values obtained with each experimental group.

FIG. 4-8: Expression of PDK4 in the hepatic tissue of the db/db mouse, after 28 days of treatment with compound 1 and compound 3, administered at 50 mpk FIG. 4-9: Expression of UCP2 (uncoupling protein 2) in the skeletal muscle tissue of the db/db mouse, after 28 days of treatment with compound 1 and compound 3, administered at 50 mpk FIG. 5: In Vitro Evaluation of the Anti-Inflammatory Properties of the Compounds According to the Invention by Measuring the Secretion of MCP1 by Monocytes, Treated with Compounds According to the Invention and Stimulated with PMA The anti-inflammatory effects of the compound according to the invention is evaluated by measuring the secretion of MCP1 (Monocyte chemotactic protein-1) by THP1 monocytes treated for 24 hours with the compounds according to the invention and stimulated simultaneously with PMA (Phorbol 12-myristate 13-acetate, which promotes an inflammatory response in cells and their differentiation into macrophages). The less MCP-1 is secreted, the more the compound according to the invention inhibits the inflammatory reaction.

STATISTIC ANALYSES

The statistical studies consist of a Student's t-test ($°/°°/°°°$) and/or a univariate ANOVA analysis of variance, followed by Tukey test (*//*). The results are compared to a control group according to the value of parameter p: $°/*$: $p<0.05$; $°°/$: $p<0.01$; $°°°/*$: $p<0.001$.

EXAMPLES

Classical reagents and catalysts are commercially available (Aldrich, Alfa Aesar, Acros, Fluka or Lancaster).

Nuclear magnetic resonance spectra of proton (NMR $^1$H) were measured on a Bruker AC300P spectrometer. Chemical shifts were expressed in ppm (parts per million) and the splitting of the NMR signals were described by with the usual abbreviations.

Example 1

General Procedure for the Synthesis of the Compounds According to the Invention Most of the compounds according to the invention were obtained specifically by reduction, following one of the procedures mentioned below, using the compounds claimed and/or described in US2005176808 patent.

The other compounds were easily obtained following similar, well-known preparation methods accessible to the person skilled in the art.

General procedure A: Reduction of Diphenylpropen-2-Ones with Triethylsilane

To a solution of diphenylpropan-2-one in dichloromethane were added triethylsilane then trifluoroacetic acid drop by drop (7.5 equivalents). The reaction mixture was stirred at room temperature and the reaction follow-up was performed by thin layer chromatography. The reaction mixture was washed with water. The aqueous layer was extracted with dichloromethane. The combined organic layers were dried over magnesium sulfate and concentrated in vacuo. The residue was column chromatographed (preparative HPLC, lichrospher (Merck) RP18 12 μm 100 Å, column: 25*250 mm).

General Procedure B: Reduction of Diphenylpropen-2-Ones with Tetrachlorosilane

To a solution of diphenylpropan-2-one in acetonitrile were added sodium iodide then tetrachlorosilane drop by drop. The reaction mixture is stirred at room temperature and the reaction follow-up was performed by thin layer chromatography. After 30 minutes to 2 hours, the mixture was partitioned between chloroform and water. The aqueous layer was extracted with chloroform. The combined organic layers were dried over sodium sulfite, then dried over magnesium sulfate and concentrated in vacuo. The residue was column chromatographed (preparative HPLC, lichrospher (Merck) RP18 12 μm 100 Å, column: 25*250 mm).

General Procedure C: Reduction of Diphenylpropen-2-Ones with Palladium on Carbon To a solution of diphenylpropen-2-one in ethanol was added a catalytic amount of palladium on carbon (10%). The reaction mixture is stirred at room temperature under hydrogen at normal pressure. The catalyst was filtered, the filtrate was concentrated in vacuo. The residue was column chromatographed.

General Procedure D: Alcohol Synthesis

To a solution of diphenylpropan-3-one in ethanol was added sodium borohydride. The reaction mixture stirred for 16 hours at 50° C. (122° F.). After cooling down, the reaction mixture was hydrolyzed and concentrated in vacuo. The residue was partitioned between dichloromethane and diluted hydrochloric acid solution.

The organic layer was washed with water, dried over magnesium sulfate and concentrated in vacuo. The residue was column chromatographed (Preparative HPLC, lichrospher (Merck) RP18 12 μm 100 Å, column: 25*250 mm).

General Procedure E: Ether Synthesis

A solution of iphenylpropan-3-ol in a ⅓:⅔ water/alcohol mixture in presence of a catalytic amount of trifluoroacetic acid was stirred for 16 hours at 60° C. The reaction mixture was then concentrated in vacuo. The residue was column chromatographed (Preparative HPLC, lichrospher (Merck) RP18 12 μm 100 Å, column: 25*250 mm).

General Procedure F: Synthesis Using Oximes and Oxime Ethers

To a solution of diphenylpropan-3-one in pyridine was added the O-alkylhydroxylamine hydrochloride. After 16 hours of reflux, the reaction mixture was concentrated in vacuo. The residue was column chromatographed.

Example 2

Synthesis of the Compounds According to the Invention

Compound 1: 2-[2,6-dimethyl-4-[3-[4-(trifluoromethoxy)phenyl-]3-oxo-propyl]phenoxy]-2-methylpropanoic acid

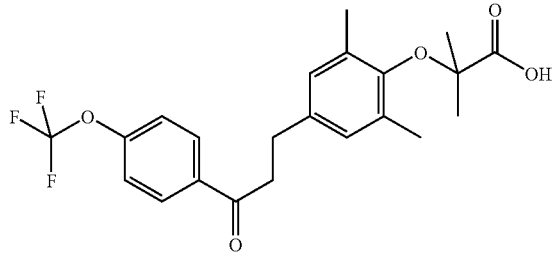

This compound was prepared following the general procedure B, using 2-[2,6-dimethyl-4-[3-[4-(trifluoromethoxy)phenyl]-3-oxo-prop-2-enyl]phenoxy]-2-methylpropanoic acid, 15 equivalent amounts of sodium iodide and 15 equivalent amounts of tetrachlorosilane;

Appearance: white solid; F=64-66° C.

NMR $^1$H (300 MHz, CDCl$_3$, δ ppm): 1.52 (s, 6H), 2.22 (s, 6H), 2.96 (t, 2H, J=7.51 Hz), 3.26 (t, 2H, J=7.51 Hz), 6.87 (s, 2H), 7.28 (d, 2H, J=8.61 Hz), 8.01 (d, 2H, J=8.61 Hz).

MS(ES-MS): 423.3 (M−1).

Compound 2: 2-[2,6-dimethyl-4-[3-[4-(trifluoromethylthio)phenyl]-3-oxo-propyl]phenoxy]-2-methylpropanoic acid

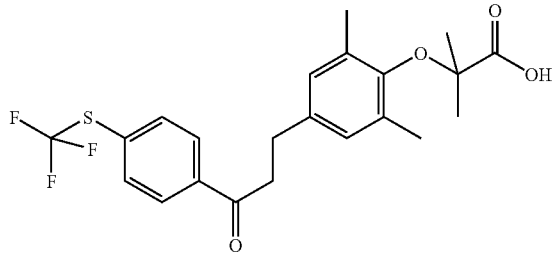

This compound was prepared following the general procedure A using 2-[2,6-dimethyl-4-[3-[4-(trifluoromethylthio)phenyl]-3-oxo-prop-2-enyl]phenoxy]-2-methylpropanoic acid and one equivalent amount of triethylsilane;

Appearance: white solid; F=83-85° C.

NMR $^1$H (300 MHz, CDCl$_3$, δ ppm): 1.52 (s, 6H), 2.23 (s, 6H), 2.97 (t, 2H, J=7.59 Hz), 3.29 (t, 2H, J=7.59 Hz), 6.88 (s, 2H), 7.74 (d, 2H, J=8.46 Hz), 7.99 (d, 2H, J=8.46 Hz).

MS(ES-MS): 439.2 (M−1).

Compound 3: 2-[2,6-dimethyl-4-[3-[4-bromophenyl]-3-oxo-propyl]phenoxy]-2-methylpropanoic acid

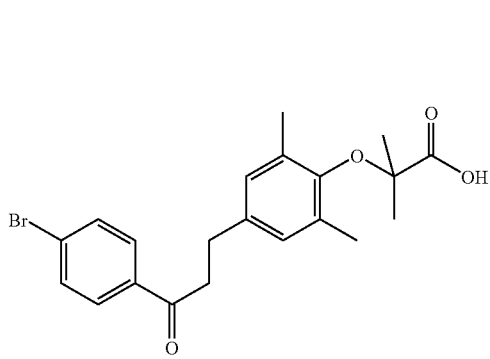

This compound was prepared following the general procedure A, using 2-[2,6-dimethyl-4-[3-[4-bromophenyl]-3-oxo-prop-2-enyl]phenoxy]-2-methyl-propanoic acid and one equivalent amount of triethylsilane;

Appearance: white viscous oil.

NMR $^1$H (300 MHz, CDCl$_3$, δ ppm): 1.52 (s, 6H), 2.23 (s, 6H), 2.96 (t, 2H, J=7.60 Hz), 3.24 (t, 2H, J=7.02 Hz), 6.89 (s, 2H), 7.61 (d, 2H, J=8.46 Hz), 7.83 (d, 2H, J=8.46 Hz).

MS(ES-MS): 417.2 (M−1) $^{79}$Br and 419.2 (M−1) $^{81}$Br.

Compound 4: 2-[2,6-dimethyl-4-[3-[4-(trifluoromethyl)phenyl]-3-oxo-propyl]phenoxyl]-2-methylpropanoic acid

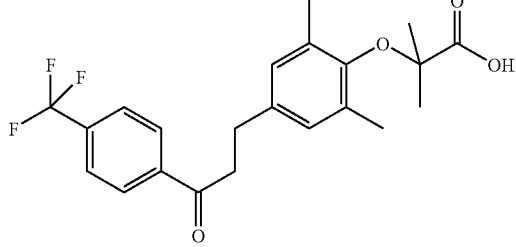

This compound was prepared following the general procedure A, using 2-[2,6-dimethyl-4-[3-[4-(trifluoromethyl)phenyl]-3-oxo-prop-2-enyl]phenoxy]-2-methyl-propanoic acid and one equivalent amount of triethylsilane;

Appearance: yellowish viscous oil.

NMR $^1$H (300 MHz, CDCl$_3$, δ ppm): 1.52 (s, 6H), 2.23 (s, 6H), 2.98 (t, 2H, J=7.29 Hz), 3.30 (t, 2H, J=7.29 Hz), 6.88 (s, 2H), 7.72 (d, 2H, J=8.17 Hz), 8.06 (d, 2H, J=8.17 Hz).

MS(ES-MS): 407.4 (M−1).

Compound 5: 2-[4-[3-[4-chloro-2-hydroxyphenyl]-3-oxo-propyl]phenylthio]-2-methylpropanoic acid

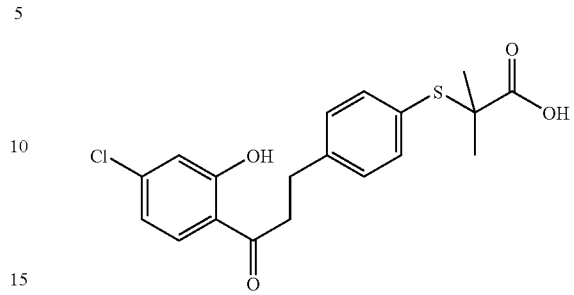

This compound was prepared following the general procedure B, using 2-[4-[3-[4-chloro-2-hydroxyphenyl]-3-oxo-prop-2-enyl]phenylthio]-2-methylpropanoic acid, and 5 equivalent amounts of sodium iodide and 5 equivalent amounts of tetrachlorosilane;

Appearance: white solid; F=136-137° C.

NMR $^1$H (300 MHz, CDCl$_3$, δ ppm): 1.52 (s, 6H), 3.08 (t, 2H, J=7.59 Hz), 3.30 (t, 2H, J=7.59 Hz), 6.87 (dd, 1H, J=1.89 Hz, J=8.79 Hz), 7.02 (d, 1H, J=1.89 Hz), 7.22 (d, 2H, J=7.89 Hz), 7.47 (d, 2H, J=8.19 Hz), 7.66 (d, 1H, J=8.46 Hz), 12.38 (s, 1H).

MS(ES-MS): 377.01 (M−1).

Compound 6: 2-[2-methyl-4-[3-[4-(3,3,3-trifluoropropyloxy)phenyl]-3-oxo-propyl]phenoxy]-2-methylpropanoic acid

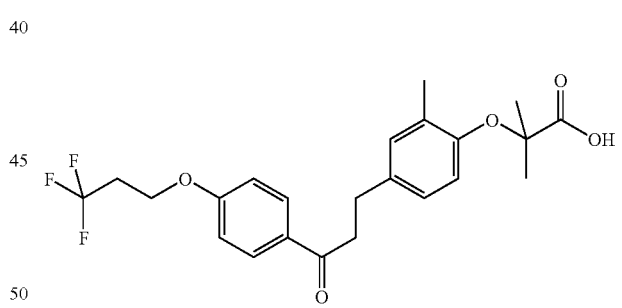

This compound was prepared by reduction following the general procedure C, using 2-(4-(3-(4-hydroxyphenyl)-3-oxo-prop-1-enyl)-2-methylphenoxy)-2-methylpropanoic acid tertiobutyl ester followed by the O-alkylation of the phenol and the acidolysis of the tertiobutyl ester according to the procedure described in US 2005/176808.

Appearance: colorless viscous oil.

NMR $^1$H (300 MHz, CDCl$_3$, δ ppm): 1.60 (s, 6H); 2.23 (s, 3H); 2.61-2.70 (m, 2H); 2.95-2.99 (m, 2H); 3.19-3.24 (m, 2H); 4.26 (t, 2H, J=6.5 Hz); 6.77 (d, 1H, J=8.5 Hz); 6.93 (d, 2H, J=8.9 Hz); 6.93-6.98 (m, 1H); 7.06 (d, 1H, J=2.1 Hz); 7.95 (d, 2H, J=8.9 Hz).

MS(ES-MS): 437.3 (M−1).

Compound 10: 2-[4-(3-methoxy-3-(4-(trifluoromethoxy)phenyl)propyl)-2,6-dimethylphenoxy]-2-methylpropanoic acid

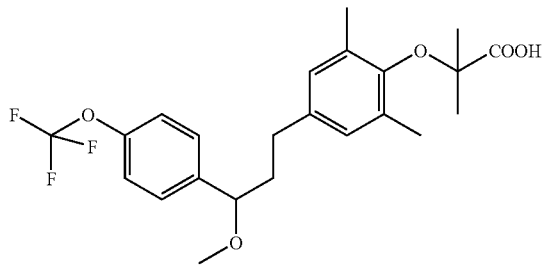

This compound was prepared following the general procedure E, using a solution of 2-(4-(3-hydroxy-3-(4-(trifluoromethoxy)phenyl)propyl)-2,6-dimethylphenoxy)-2-methylpropanoic acid in a ⅓:⅔ mixture of water/methanol.

Appearance: colorless viscous oil.

NMR $^1$H (300 MHz, CDCl$_3$, δ ppm): 1.46 (s, 6H); 1.91-2.21 (m, 2H); 2.15 (s, 6H); 2.49-2.69 (m, 2H); 3.83 (s, 3H); 4.69 (dd, 1H, J=7.7 Hz, J=5.1 Hz); 6.78 (s, 2H); 7.19 (d, 2H, J=8.5 Hz); 7.36 (d, 2H, J=8.5 Hz).

MS(ES-MS): 458.3 (M+NH$_4^+$), 463.2 (M+Na$^+$), 479.2 (M+K$^+$).

Compound 12: 2-(2,6-dimethyl-4-(3-oxo-3-(4-(2,2,2-trifluoroethoxy)phenyl)propyl)phenoxy)-2-methylpropanoic acid

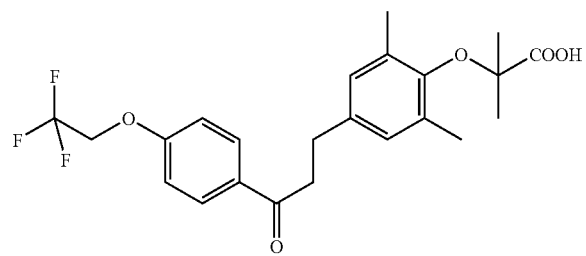

This compound was prepared by reduction following the general procedure C, using 2-(4-(3-(4-hydroxyphenyl)-3-oxo-prop-1-enyl)-2,6-dimethylphenoxy)-2-methylpropanoic acid tertiobutyl ester, followed by the O-alkylation of the phenol and the acidolysis of the tertiobutyl ester according to the procedure described in the US2005176808 patent.

Appearance: white solid; F=98-99° C.

NMR $^1$H (300 MHz, CDCl$_3$, δ ppm): 1.45 (s, 6H); 2.17 (s, 6H); 2.89 (m, 2H); 3.18 (m, 2H); 4.40 (q, 2H, J=8.1 Hz); 6.82 (s, 2H); 6.95 (d, 2H, J=9.1 Hz); 7.93 (d, 2H, J=9.1 Hz).

MS(ES-MS): 437.4 (M−1).

Compound 17: 2-(4-(3-(2-fluoro-4-(2,2,2-trifluoroethoxy)phenyl)-3-oxo-propyl)-2,6-dimethylphenoxy)-2-methylpropanoic acid

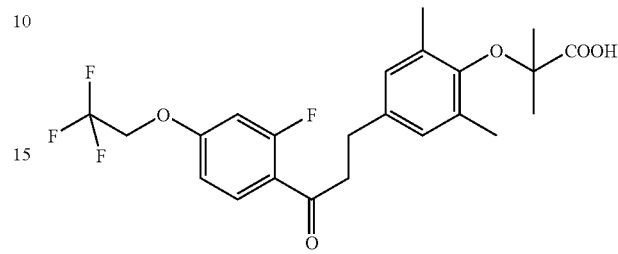

This compound was prepared by reduction following the general procedure C, using 2-(4-(3-(2-fluoro-4-hydroxyphenyl)-3-oxo-prop-1-enyl)-2,6-dimethylphenoxy)-2-methylpropanoic acid tertiobutyl ester, followed by the O-alkylation of the phenol and the acidolysis of the tertiobutyl ester in accordance with patent US2005176808.

Appearance: colorless viscous oil.

NMR $^1$H (300 MHz, CDCl$_3$, δ ppm): 1.51 (s, 6H); 2.21 (s, 6H); 2.92 (t, 2H, J=7.6 Hz); 3.23 (td, 2H, J=7.6 Hz J=3.1 Hz); 6.70 (dd, J=8.7 Hz J=2.3 Hz); 6.81 (dd, J=12.6 Hz J=2.3 Hz); 6.86 (s); 7.91 (t, 1H, J=8.7 Hz).

MS(MALDI-TOF): 479 (M+Na$^+$).

Compound 30: 2-[4-(3-hydroxy-3-(4-(trifluoromethoxy)phenyl)propyl)-2,6-dimethylphenoxy]-2-methylpropanoic acid

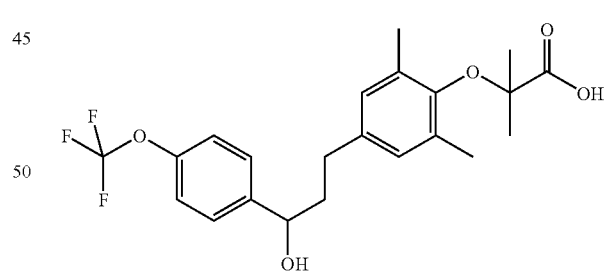

This compound was prepared following the general procedure D, using 2-[2,6-dimethyl-4-[3-[4-(trifluoromethyloxy)phenyl]-3-oxo-propyl]phenoxy]-2-methylpropanoic acid, and 4 equivalent amounts of sodium borohydride.

Appearance: colorless viscous oil.

NMR $^1$H (300 MHz, CDCl$_3$, δ ppm): 1.46 (s, 6H); 1.94-2.10 (m, 2H); 2.17 (s, 6H); 2.46-2.66 (m, 2H); 4.69 (dd, 1H, J=7.6 Hz J=5.5 Hz); 6.78 (s, 2H); 7.17 (d, 2H, J=8.3 Hz); 7.34 (d, 2H, J=8.3 Hz).

MS(ES-MS): 425.3 (M−1).

Compound 33: 2-(4-(3-(methoxyimino)-3-(4-(trifluoromethoxy)phenyl)propyl)-2,6-dimethylphenoxy)-2-methylpropanoic acid

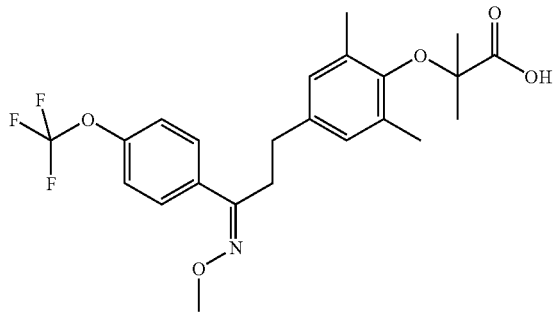

This compound was prepared following the general procedure F, using 2-[2,6-dimethyl-4-[3-[4-(trifluoromethoxy)phenyl]-3-oxo-propyl]phenoxy]-2-methylpropanoic acid.

Appearance: yellowish viscous oil.

NMR $^1$H (300 MHz, CDCl$_3$, δ in ppm): 1.49 (s, 6H), 2.21 (s, 6H), 2.71-2.77 (m, 2H), 2.95-3.01 (m, 2H), 4.01 (s, 3H), 6.82 (s, 2H), 7.17 (d, 2H, J=8.7 Hz), 7.59 (d, 2H, J=8.7 Hz). MS(ES-QTOF): 476 (M+Na$^+$).

Compound 35: 2-(2,6-dimethyl-4-(3-oxo-3-(4-(trifluoromethoxy)phenyl)propyl)phenoxy)-2-methylpropanoic acid tertiobutyl ester

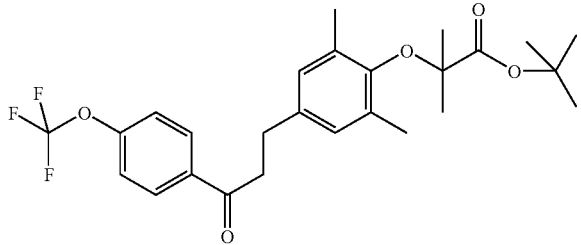

This compound was prepared by reduction following the general procedure C, using 3-(4-hydroxy-3,5-dimethylphenyl)-1-(4-(trifluoromethoxy)phenyl)propan-1-one, followed of the O-alkylation of the phenol and the acidolysis of the tertiobutyl ester according to the US2005176808 patent.

Appearance: colorless viscous oil.

NMR $^1$H (300 MHz, CDCl$_3$, δ ppm): 1.42 (s, 6H); 1.51 (s, 9H); 2.21 (s, 6H); 2.94 (t, 2H, J=7.9 Hz); 3.25 (t, 2H, J=7.9 Hz); 6.82 (s, 2H); 7.28 (d, 2H, J=9.1 Hz); 8.01 (d, 2H, J=9.1 Hz).

The other compounds were obtained following procedures similar to the procedures A to F. and easy to implement for the person skilled in the art.

Example 3

In Vitro Evaluation of the PPAR Activating Properties of the Compounds According to the Invention The PPAR activating properties of the compounds according to the invention are evaluated in vitro.

Principle

The activation of PPARs is evaluated in vitro using a monkey kidney fibroblast line (COS-7), by measuring the transcriptional activity of chimeras made up of the DNA binding domain of the Gal4 transcription factor of yeast and the binding domain to the ligand of the different PPARs. The compounds are tested at doses of between $10^{-7}$ and 100 μM on Gal4-PPARα, γ, and δ chimeras.

Protocol

Culture of the Cells

COS-7 cells come from ATCC (American type culture collection) and are cultivated in a DMEM (Dulbecco's modified eagle's medium) medium supplemented with 10% (vol/vol) of fetal calf serum, 100 U/ml of penicillin (Gibco, Paisley, UK) and 2 mM of L-Glutamine (Gibco, Paisley, UK). Cells are incubated at 37° C. in a humid atmosphere containing 5% CO$_2$.

Description of the Plasmids Used in Transfection

The plasmids Gal4(RE)_TkpGL3, pGal4-hPPARα, pGal4-hPPARγ, pGal4-hPPARδ and pGal4-φ have been described in the literature (Raspe E et al., 1999). The constructions pGal4-hPPARα, pGal4-hPPARγ, and pGal4-hPPARδ were obtained by cloning, in the pGal4-φ vector, of DNA fragments amplified by PCR and corresponding to the DEF domains of human PPARα, PPARγ, and PPARδ nuclear receptors.

Transfection

The COS-7 cells in suspension are transfected with 150 ng of DNA per well, with a pGal4-PPAR/Gal4(RE)_TkpGL3 ratio of 1/10, in presence of 10% fetal calf serum. The cells are plated in 96-well plates (4×10$^4$ cells/well), then are incubated for 24 hours at 37° C. Activation with the test compounds is performed for 24 hours at 37° C. in a medium without serum. At the end of the experiment, the cells are lysed and the luciferase activity is determined using Steady-Lite™ HTS (Perkin Elmer) or Steady Glow Luciferase (Promega) in accordance with the provider's recommendations.

Results

The compounds according to the invention were tested on 3 PPAR isoforms. The results obtained with compounds 1, 2, 3, 4, 5, and 7 are detailed in FIGS. (1-1) to (1-18).

The inventors have shown the significant and dose-dependent augmentation of luciferase activity in the cells transfected with the plasmids pGal4-hPPAR and treated with the compounds according to the invention.

Unexpectedly, the presented experimental data show that, in vitro, the compounds according to the invention bind to PPARs in vitro and induce an activation of the transcriptional activity.

Example 4

In Vivo Evaluation, on ApoE2/E2 Mouse, of Body-Weight Properties, of Hypolipidemic Properties, and Properties Stimulating the Synthesis of HDL-Cholesterol of the Compounds According to the Invention Principle The properties effecting body weight and hypolipidemic properties of the compounds according to the invention are evaluated in vivo by measuring the body weight and the plasmatic lipids, and by analyzing the gene expression of gene target of PPARs, after a treatment of the dyslipidemic E2/E2 mouse with the compounds according to the invention.

The murine model used is the ApoE2/E2 mouse, a transgenic mouse having the human apolipoprotein E isoform E2

(Sullivan P M et al., 1998). In human, this apolipoprotein, a constituent of low and very low density lipoproteins (LDL-VLDL), is present in three isoforms E2, E3, and E4. The E2 form presents a mutation affecting the amino acid of position 158, which considerably weakens the affinity of this protein for the receptors to LDL receptors. Accordingly, the VLDL clearance is nearly non-existent. An accumulation of low-density lipoproteins then occurs along with a mixed hyperlipidemia known as of type III (high cholesterol and triglycerides rates).

PPARα regulates the expression of genes involved in the transport of lipids (apolipoproteins such as Apo AI, Apo AII, and Apo CIII, membrane transporters such as FAT) and the catabolism of lipids (ACO, CPT-I, or CPT-II, fatty acid β-oxidation enzymes). Accordingly, a treatment with PPARα activators, in human as well as in rodents, leads to a reduction in the circulating triglycerides level. Measuring the plasmatic lipids rate, after a treatment with the compounds according to the invention, allows to evaluate the PPAR agonist properties and the hypolipidemic effect of the compounds according to the invention.

The treatment with PPAR activators, in human as in rodents, also leads sometimes to an elevation of the plasma HDL-cholesterol rate. Measuring the plasma HDL-cholesterol rate, therefore, allows to show the stimulative effect of compounds according to the invention on HDL-cholesterol synthesis.

The agonist properties of PPARα previously measured in vitro should, in the liver, lead to an over-expression of the target genes directly under the control of the PPARα. The genes we have studied in this experiment are Apo CIII (an apolipoprotein involved in lipid metabolism), and PDK-4 (a an enzyme involved in glucid metabolism enzyme). Measuring the transcriptional activity of PPARα target genes, after a treatment with compounds according to the invention, does therefore allow to evaluate the hypolipidemic properties of the compounds according to the invention.

Protocol

Treatment of the Animals

The ApoE2/E2 transgenic mice were kept on a 12 hour/12 hour light/dark cycle at a constant temperature of 20±3° C. After a one week acclimatization period, the mice were weighed and divided into groups of 6 animals selected so as to render uniform the distribution of their body weights and plasma lipid rates, determined before the experiment. The tested compounds were suspended in carboxymethylcellulose (Sigma C4888) and administered by intra-gastric tube feeding, once a day for 8 days at the chosen dosage. The animals had free access to food and water (standard diet). Taking of food and weight gain are recorded throughout the experiment. At the end of the experiment, the animals were anesthetized after a 4 hour fast, a blood sample was taken using (EDTA) anticoagulant, then the mice were weighed and euthanized. The plasma was prepared by centrifugation at 3000 rotations/minute for 20 minutes. The samples were kept at +4° C.

Liver samples were removed, frozen in liquid nitrogen, and then kept at −80° C. for subsequent analyses.

Measurement of Plasma Lipids

Plasma lipid concentrations (total cholesterol and triglycerides) are measured by enzymatic dosages (bioMérieux-Lyon-France) according to the provider's recommendations.

Plasma cholesterol and triglycerides rates are measured after 8 days of a per os treatment with the compounds according to the invention. These rates are compared with those obtained with control animals (not treated with compounds according to the invention). The measured difference shows the hypolipidemic effect of the compounds according to the invention.

Measurement of HDL-Cholesterol

Low-density lipoproteins (VLDL and LDL) are precipitated by Phosphotungstate. The precipitate is eliminated by centrifugation. HDL cholesterol present in the supernatant is measured by enzymatic dosages (bioMérieux-Lyon-France) in accordance with the provider's recommendations.

Gene expression analysis by quantitative RT-PCR Total RNA is extracted from liver fragments by using a NucleoSpin® 96 RNA kit (Macherey Nagel, Hoerdt, France) according to the manufacturer's instructions.

1 μg of total RNA (quantified by using the Ribogreen RNA quantification kit (Molecular Probes)) is then reverse-transcribed into complementary DNA by means of a 1 hour reaction at 37° C. in a total volume of 20 μl containing a 1× buffer (Sigma), 1.5 mM of DTT, 0.18 mM of dNTPs (Promega), 200 ng of pdN6 (Amersham), 30 U of RNase inhibitor (Sigma), and 1 μl of MMLV-RT (Sigma).

The PCR quantitative experiments were carried out using the MyiQ Single-Color Real-Time PCR Detection System (Biorad, Marnes-la-Coquette, France) and were performed using the iQ SYBR Green Supermix kit according to the manufacturer's recommendations, in 96-well plates in 5 μl of a diluted reverse transcription solution at a hybridization temperature of 55° C. The specific primer pairs of the genes studied were used:

```
                                            (SEQ ID NO: 1)
PDK4: sense primer: 5'-TACTCCACTGCTCCAACACCTG-3'
and (SEQ ID NO: 2))
antisense primer 5'-GTTCTTCGGTTCCCTGCTTG-3'

(SEQ ID NO: 3)
ApoCIII: sense primer: 5'-CTCTTGGCTCTCCTGGCATC-3'
and (SEQ ID NO: 4)
antisense primer 5'-GCATCCTGGACCGTCTTGGA-3'.
```

The quantity of fluorescence emitted is directly proportional to the quantity of cDNA present at the beginning of the reaction and amplified during the PCR. For each target studied, a range of solutions is performed with successive dilutions of a mixture made up of a few μl of different reverse-transcription solutions. The relative expression levels of each target are thus determined by using efficiency curves obtained with the points relative to the range of PCR solutions.

The expression levels of the genes of interest are then normalized regarding the one of the reference gene 36B4 (whose specific primers are: sense primer: 5'-CATGCTCAA-CATCTCCCCCTTCTCC-3' (SEQ ID NO: 7) and antisense primer: 5'-GGGAAGGTGTAATCCGTCTCCACAG-3' (SEQ ID NO: 8)).

The induction factor, i.e. the ratio between the relative signal (induced by the compound according to the invention) and the average of relative values obtained with the control group, is then calculated for each sample. The higher the induction factor is, the more the compound promotes gene expression. The final result is represented as the average of the induction values obtained with each experimental group.

Results

Body Weight

FIG. 2-1 compares the animals' weight gain after 8 days of treatment with compound 1 administered at 5, 10, and 50 mpk to the control animals' weight gain. Unexpectedly, a weight loss was measured in the animals treated with compound 1.

Measurement of Plasma Lipids

FIGS. 2-2 and 2-3 compare plasma total cholesterol and HDL-cholesterol rates after 8 days of treatment with compound 1 at 5, 10, and 50 mpk with the ones obtained with the control animals. Unexpectedly, the circulating total cholesterol rates were significantly reduced and the HDL-cholesterol rates were significantly increased by the treatment.

FIGS. 2-4 and 2-5 compare plasma triglyceride and free fatty acid rates after 8 days of treatment with compound 1 administered at 5, 10, and 50 mpk with the ones obtained from the control animals. Unexpectedly, the rates of circulating triglycerides and free fatty acids have decreased very significantly with the treatment.

Gene Expression Analysis by Quantitative RT-PCR

The inventors have also shown that the compounds according to the invention are, in vivo, regulators of PPARs target gene expression. The results presented in FIGS. 2-6 and 2-7 show that compound 1 administered at 5, 10, and 50 mpk for 8 days to E2/E2 mice, induces a significant increase in hepatic expression of the gene coding for PDK4 (FIG. 2-6) and a reduction in hepatic expression of the gene coding for ApoCIII (FIG. 2-7). All the coding genes for enzymes specifically involved in lipid and glucid metabolism and the fact that their expression is modulated by the compounds according to the invention reinforce the idea that these compounds present a great potential for the treatment of metabolic pathologies.

Conclusion

Unexpectedly, the presented experimental data show that the compounds according to the invention, in vivo, induce body weight loss and stimulate HDL cholesterol synthesis as well as a hypolipidemic effect (reduction of plasma levels of triglycerides and free fatty acids). Additionally, the presented experimental data show that the compounds according to the invention modulate the expression of genes regulated by the activation of PPARs that code for enzymes especially involved in lipid and glucid metabolism.

Example 5

In Vivo Evaluation, on the C57BI6 Mouse, of Body-Weight Properties, of Hypolipidemic Properties, and Properties Stimulating the Synthesis of HDL-Cholesterol of the Compounds According to the Invention Principle The effects of the compounds according to the invention on the body weight and their hypolipidemic properties are evaluated in vivo by measuring the body weight and the plasmatic lipids, and by analyzing the gene expression of the PPARs target genes, after a treatment of the dyslipidemic C57BI6 mouse with the compounds according to the invention.

Protocol

Treatment of the Animals

Female C57BI6 mice were kept on a 12 hour/12 hour light/dark cycle at a constant temperature of 20±3° C. After a one week acclimatization period, the mice were weighed and divided into groups of 6 animals selected such as the distribution of body weight and of plasma lipid rate, determined before the experiment, was uniform. The tested compounds were suspended in carboxymethylcellulose (Sigma C4888) and administered to the animals by gastric gavage, once a day for 14 days at the chosen doses. The animals had free access to food and water (standard diet). Taking of food and weight gain are recorded throughout the experiment. At the end of the experiment, after a 4 hour fast, the animals were anesthetized and a blood sample was taken on anticoagulant (EDTA). Then the mice were weighed and euthanized. The plasma was separated by centrifugation at 3000 rotations/minute for 20 minutes. The samples were kept at +4° C. Hepatic tissue samples were removed, frozen in liquid nitrogen, and then kept at −80° C. for later analyses.

Measurement of HDL Cholesterol

Low-density lipoproteins (VLDL and LDL) are precipitated by Phosphotungstate. The precipitate is eliminated by centrifugation. HDL-cholesterol present in the supernatant is measured by enzymatic assays (bioMérieux-Lyon-France) in accordance with the provider's recommendations.

Measurement of Plasma Triglycerides

Plasma triglyceride concentrations were measured by enzymatic assays (bioMérieux-Lyon-France) according to the provider's recommendations.

Gene Expression Analysis by Quantitative RT-PCR

Total RNA was extracted from liver fragments by using a NucleoSpin® 96 RNA kit (Macherey Nagel, Hoerdt, France) according to the manufacturer's instructions. 1 µg of total RNA (quantified by spectrophotometry) was then reverse-transcribed into cDNA by means of a 1 hour reaction at 37° C. in a total volume of 20 µl containing a 1× buffer (Sigma), 1.5 mM of DTT, 0.18 mM of dNTPs (Promega), 200 ng of pdN6 (Amersham), 30 U of RNase inhibitor (Sigma), and 1 µl of MMLV-RT (Sigma).

The PCR quantitative experiments were carried out using the MyiQ Single-Color Real-Time PCR Detection System (Biorad, Marnes-la-Coquette, France) and were performed using the iQ SYBR Green Supermix kit according to the provider's recommendations, in 96-well plates in 5 µl of a diluted reverse transcription solution and at a hybridization temperature of 55° C. The specific primer pairs of the genes studied were used:

```
                                               (SEQ ID NO: 1)
PDK4: sense primer: 5'-TACTCCACTGCTCCAACACCTG-3'
and (SEQ ID NO: 2))
antisense primer 5'-GTTCTTCGGTTCCCTGCTTG-3'

(SEQ ID NO: 3)
ApoCIII: sense primer: 5'-CTCTTGGCTCTCCTGGCATC-3'
and (SEQ ID NO: 4)
antisense primer 5'-GCATCCTGGACCGTCTTGGA-3'.
```

The amount of fluorescence emitted is directly proportional to the amount of cDNA present at the beginning of the reaction and amplified during the PCR. For each target studied, a range of solutions is performed with successive dilutions of a mixture made up of a few µl of different reverse-transcription solutions. The relative levels of expression of each target are thus determined by using efficiency curves obtained with the points relative to the range.

The expression levels of the genes of interest were then normalized regarding the level expression of the reference gene 36B4 (whose specific primers are: sense primer: 5'-CATGCTCAACATCTCCCCCTTCTCC-3' (SEQ ID NO: 7) and antisense primer: 5'-GGGAAGGTGTAATCCGTCTCCACAG-3' (SEQ ID NO: 8)).

Induction factor relative to each sample was then calculated. The higher the induction factor is, the more the compound promotes gene expression. The final result is represented as the average of the induction values obtained with each experimental group.

Results

Body Weight

FIG. 3-1 compares the animals' weight gain after 14 days of treatment with compound 1 administered at 3, 10, and 30 mpk to the control animals' weight gain. Unexpectedly, a weight loss was measured in the animals treated with compound 1.

Measurement of Plasma Lipids

FIG. 3-2 compares the rates of plasma HDL-cholesterol after 14 days of treatment with compound 1 administered at 3, 10, and 30 mpk with the rates obtained with the control. Unexpectedly, the rates of circulating HDL-cholesterol were very significantly increased thanks to the treatment.

FIG. 3-3 compares the plasma triglycerides rates after 14 days of treatment with compound 1 administered at 3, 10, and 30 mpk with the rates obtained with the control. Unexpectedly, the circulating triglycerides rates were very significantly diminished thanks to the treatment.

Genetic Expression Analysis by Quantitative RT-PCR

Figures 1, 2, 3, 4, 5:
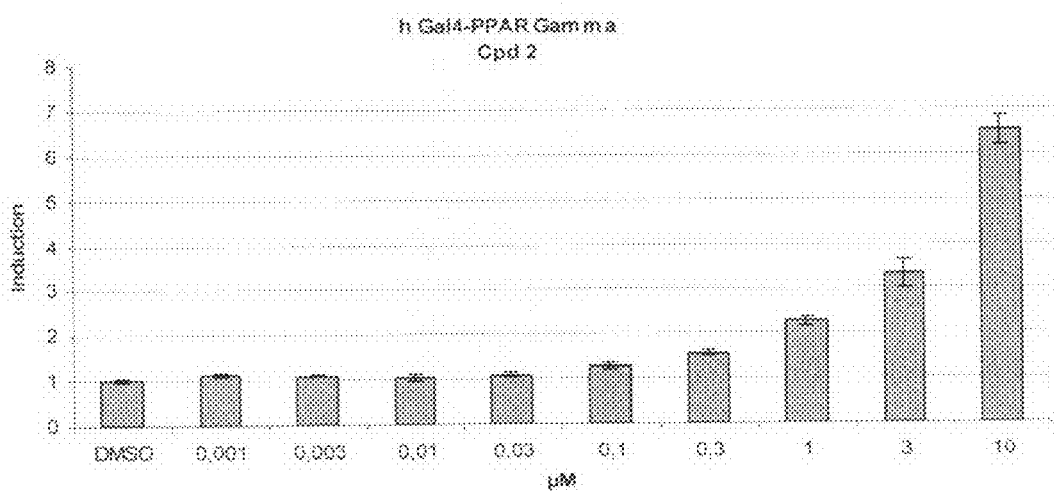
Figures 1, 2, 3, 4, 5, 6:
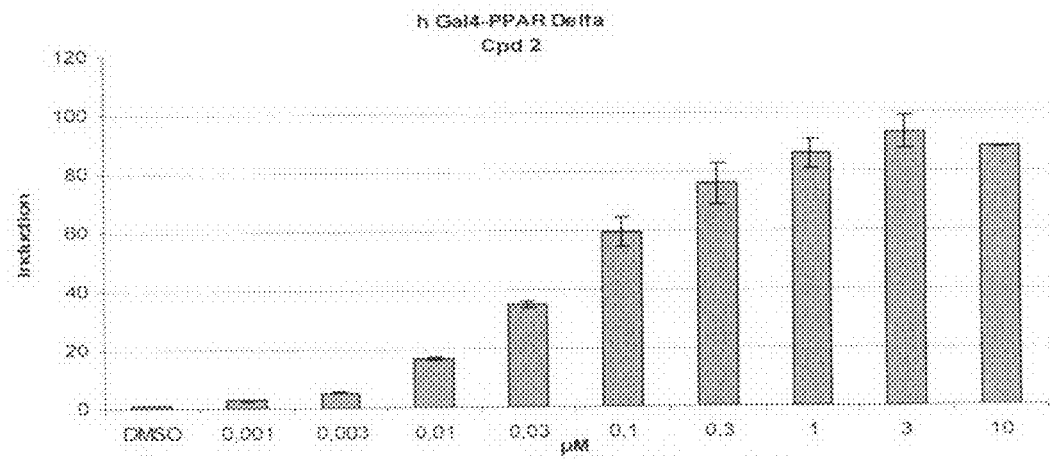
Figures 1, 2, 3, 4, 5, 6, 7:
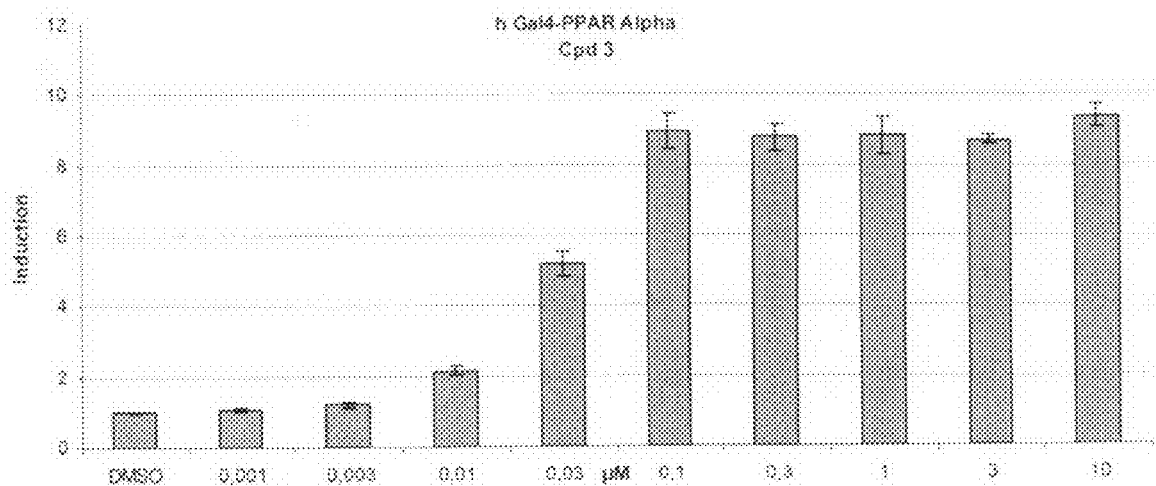
Figures 1, 2, 3, 4, 5, 6, 7, 8:
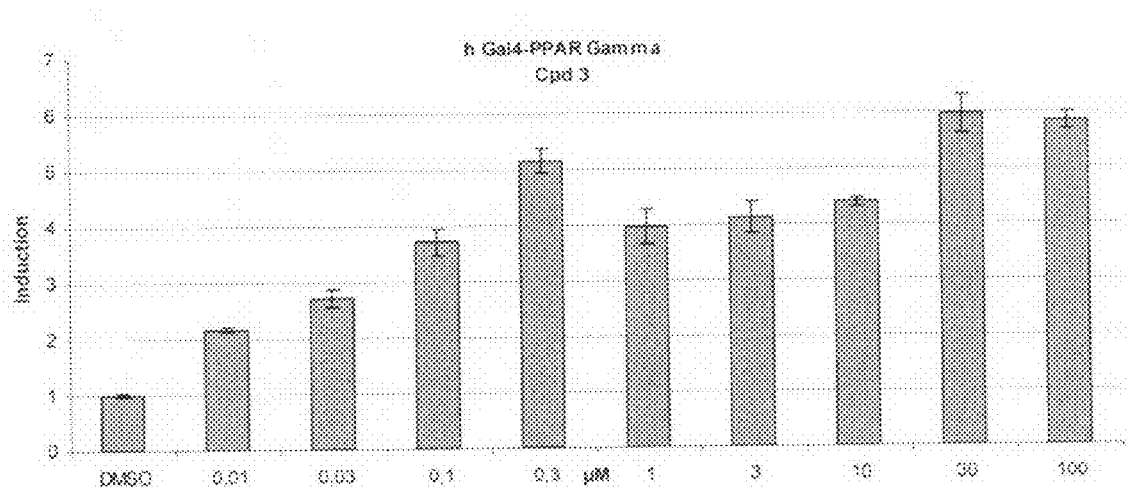
Figures 1, 2, 3, 4, 5, 6, 7, 8, 9:
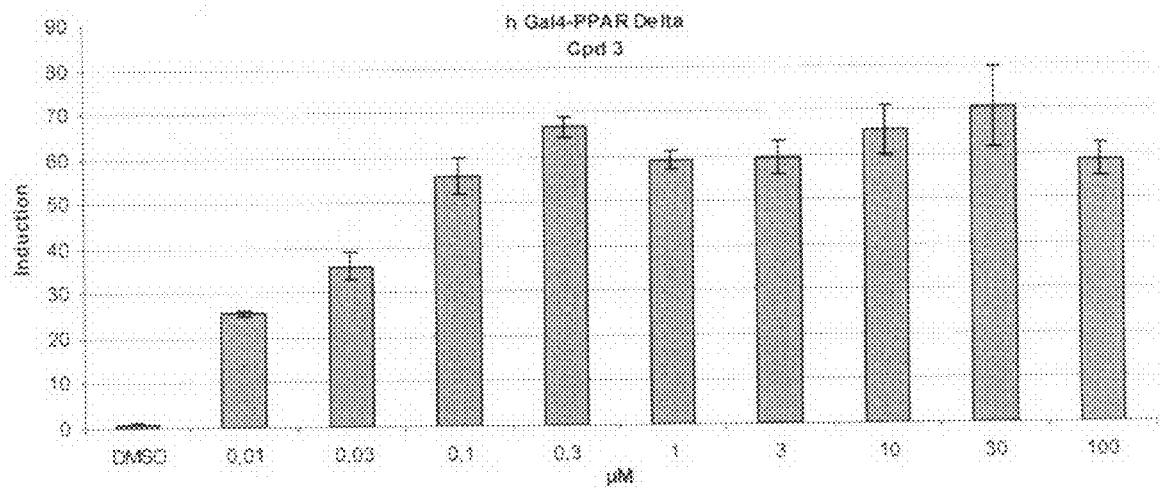
Figures 1, 2, 3, 4, 5, 6, 7, 8, 9, 10:
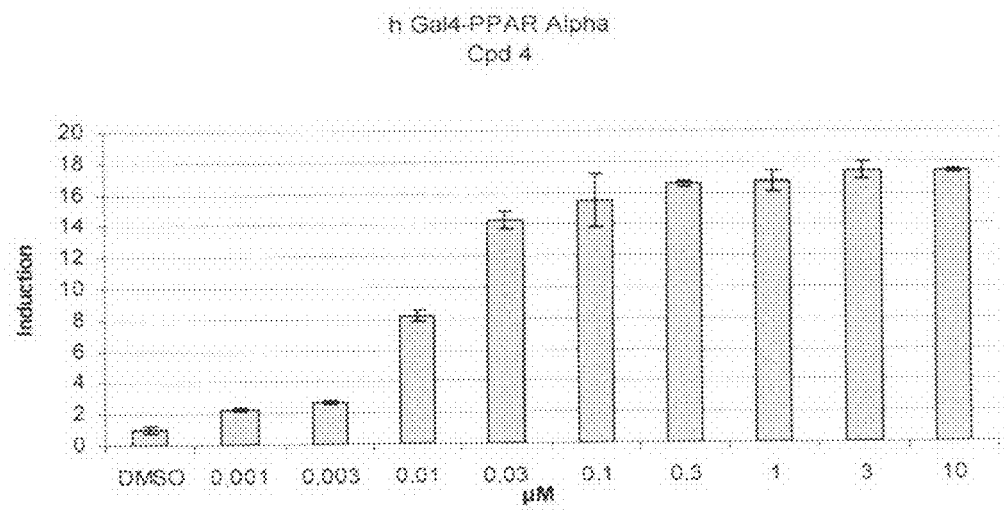
Figures 1, 2, 3, 4, 5, 6, 7, 8, 9, 10, 11:
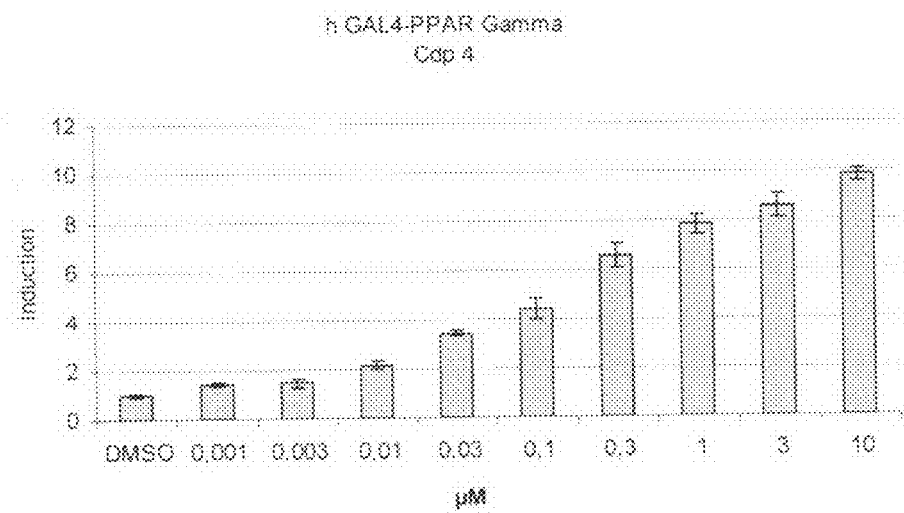
Figures 1, 2, 3, 4, 5, 6, 7, 8, 9, 10, 11, 12:
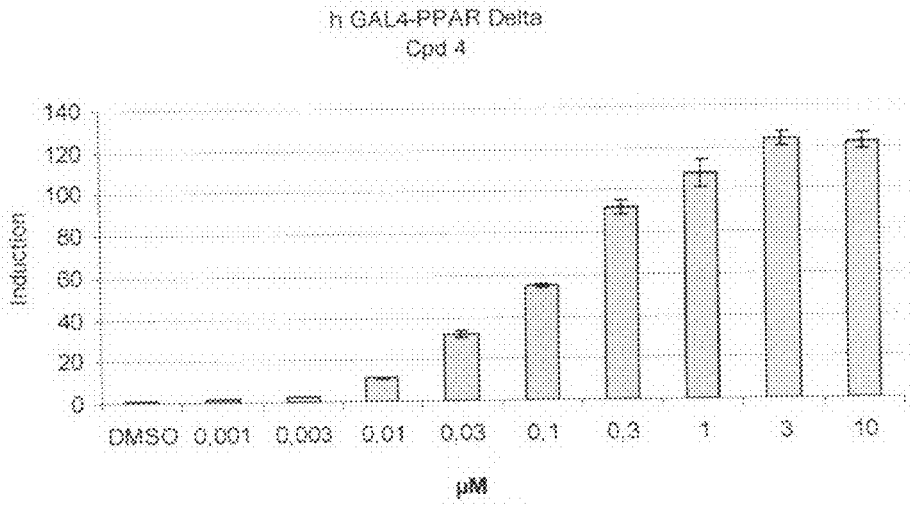
Figures 1, 2, 3, 4, 5, 6, 7, 8, 9, 10, 11, 12, 13:
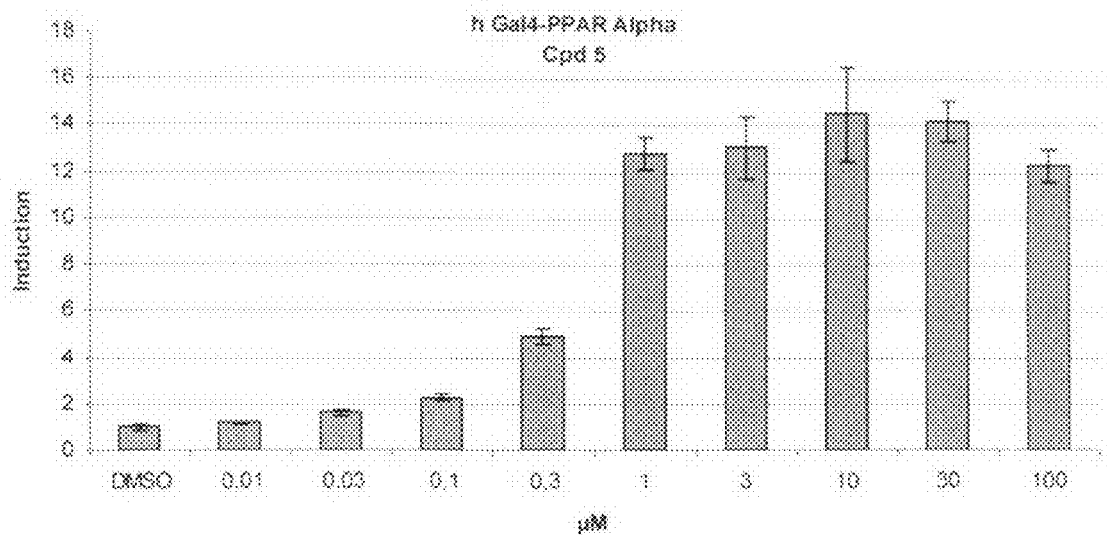
Figures 1, 2, 3, 4, 5, 6, 7, 8, 9, 10, 11, 12, 13, 14:
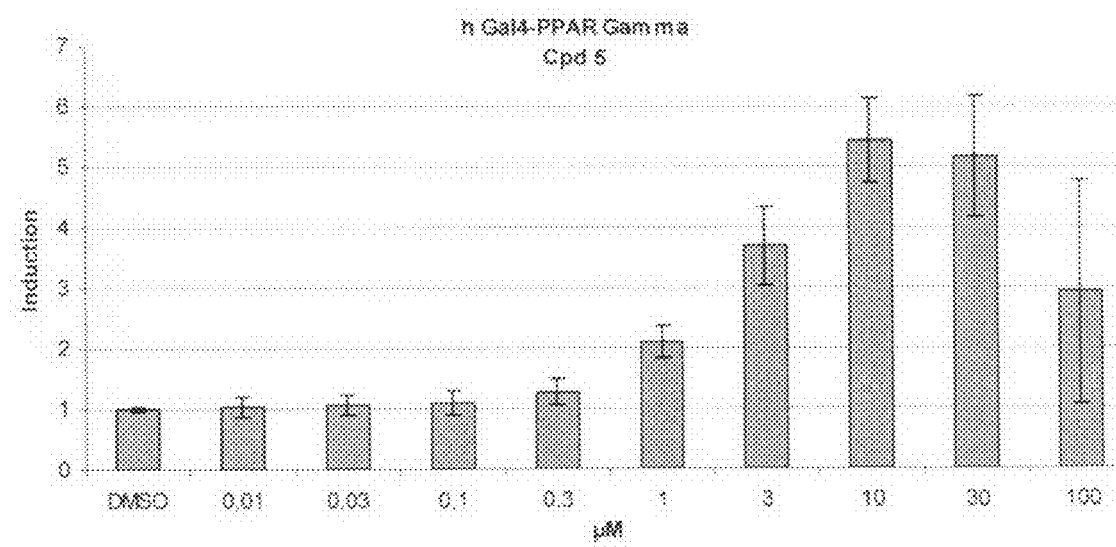
Figures 1, 2, 3, 4, 5, 6, 7, 8, 9, 10, 11, 12, 13, 14, 15:
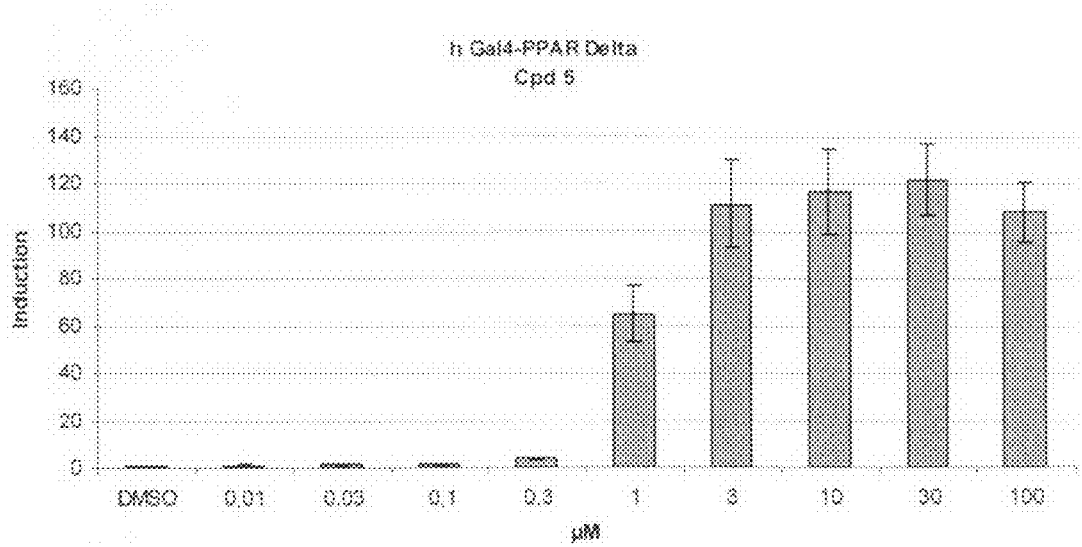
Figures 1, 2, 3, 4, 5, 6, 7, 8, 9, 10, 11, 12, 13, 14, 15, 16:
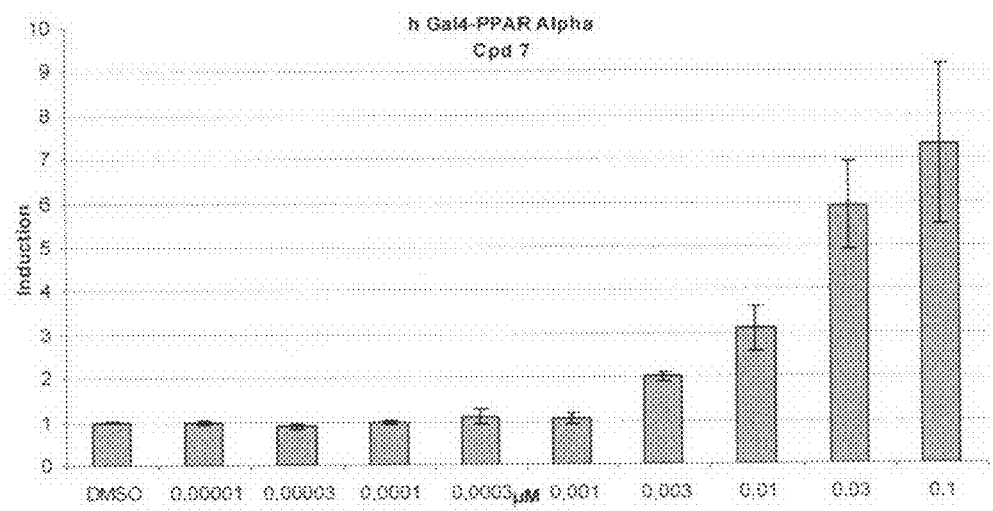
Figures 1, 2, 3, 4, 5, 6, 7, 8, 9, 10, 11, 12, 13, 14, 15, 16, 17:
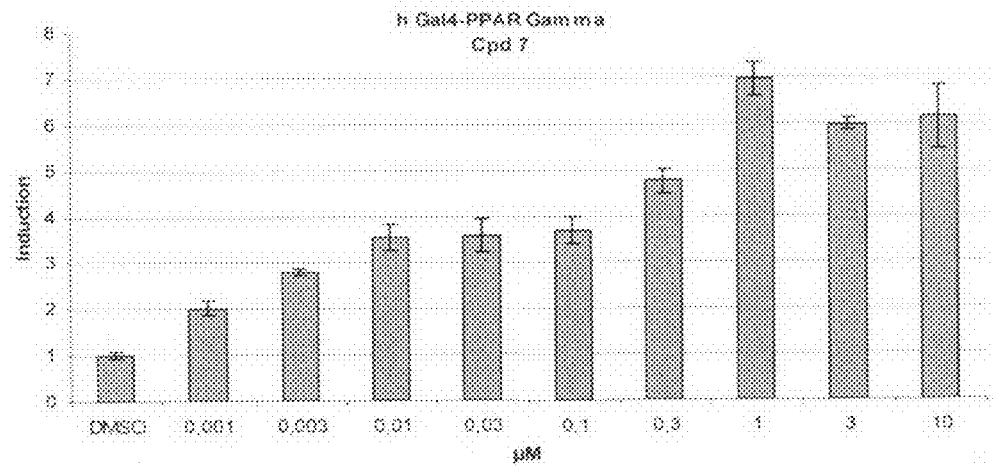
Figures 1, 2, 3, 4, 5, 6, 7, 8, 9, 10, 11, 12, 13, 14, 15, 16, 17, 18:
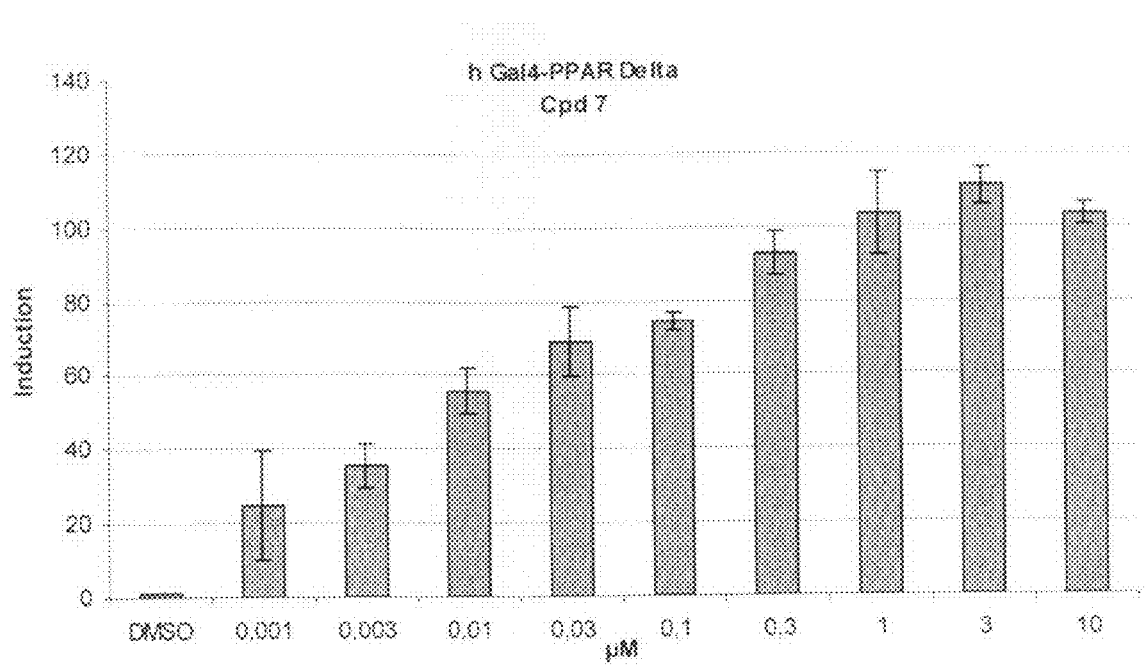
Figures 1, 2:
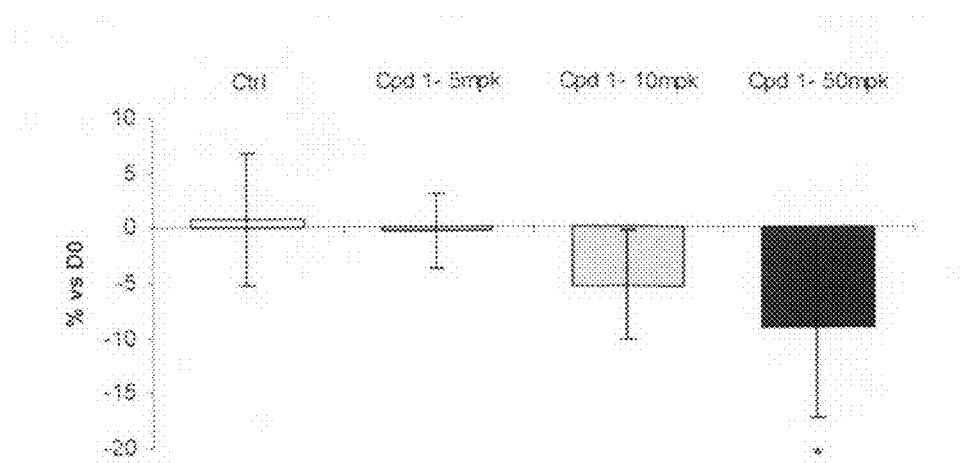
Figure 2:
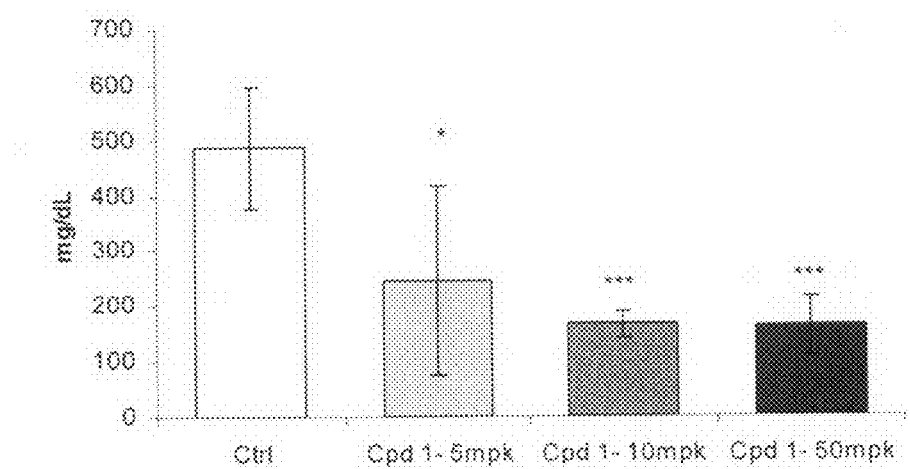
Figures 2, 3:
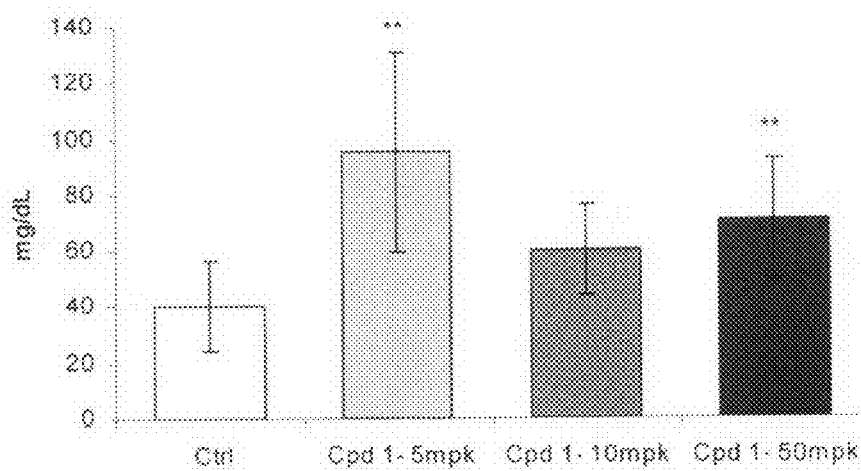
Figures 2, 3, 4:
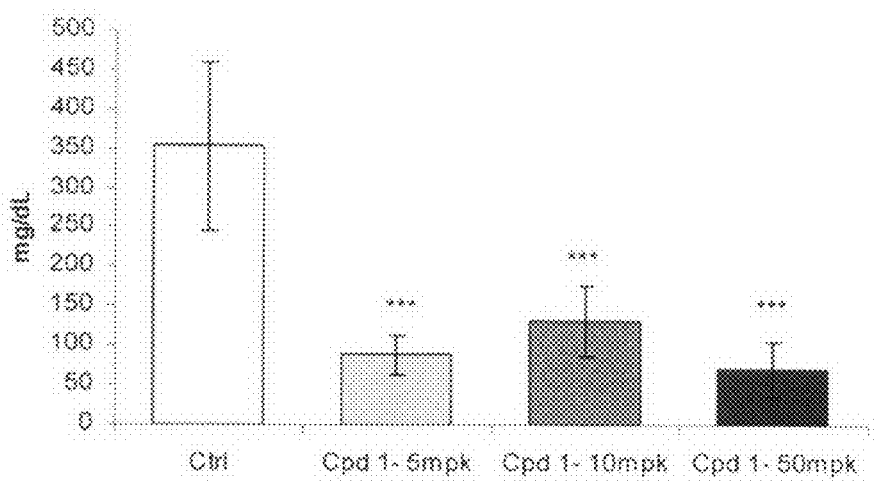
Figures 2, 3, 4, 5:
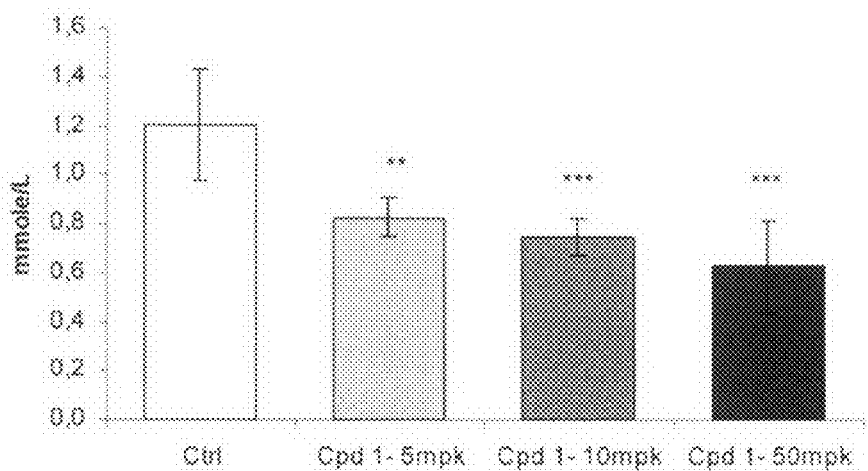
Figures 2, 3, 4, 5, 6:
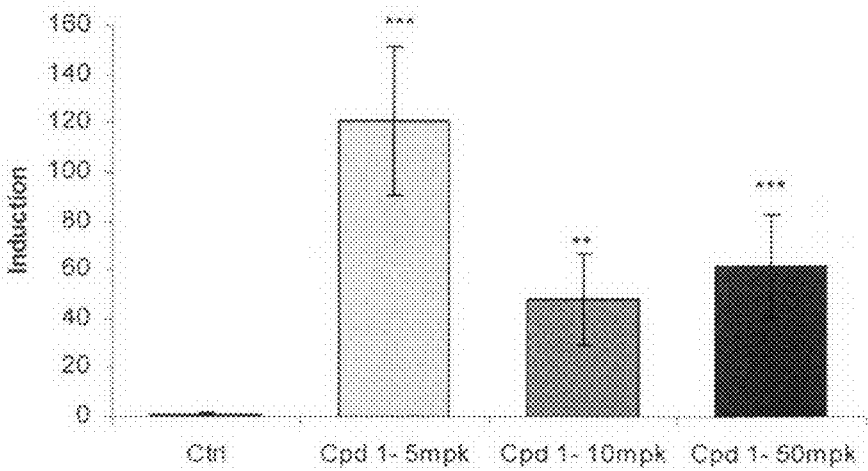
Figures 2, 3, 4, 5, 6, 7:
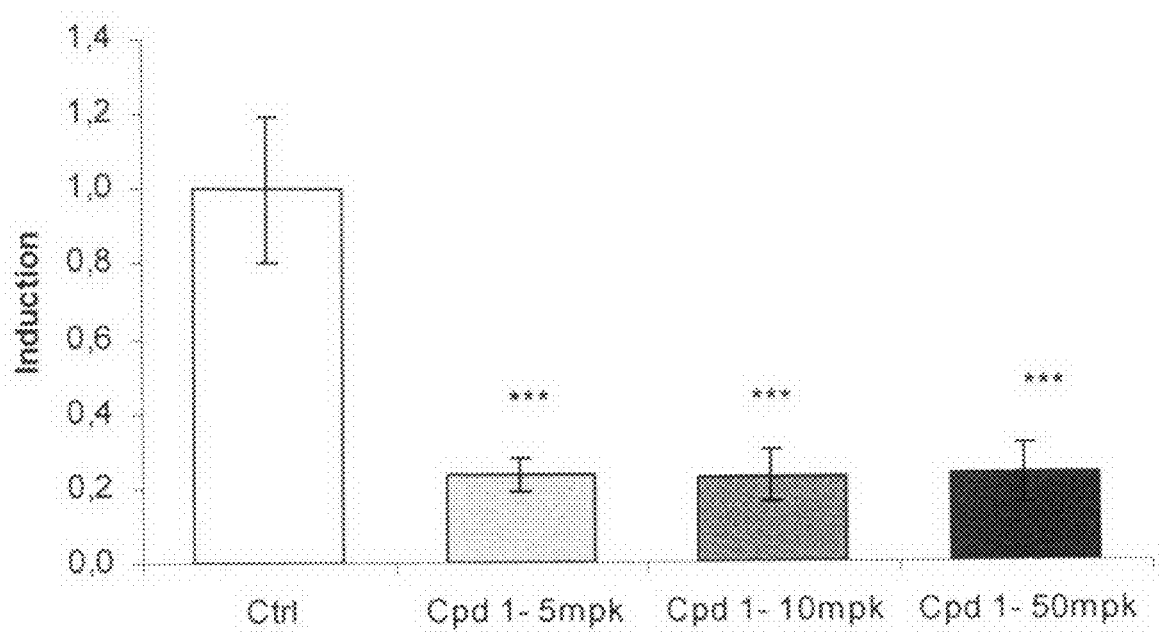
Figures 1, 3:
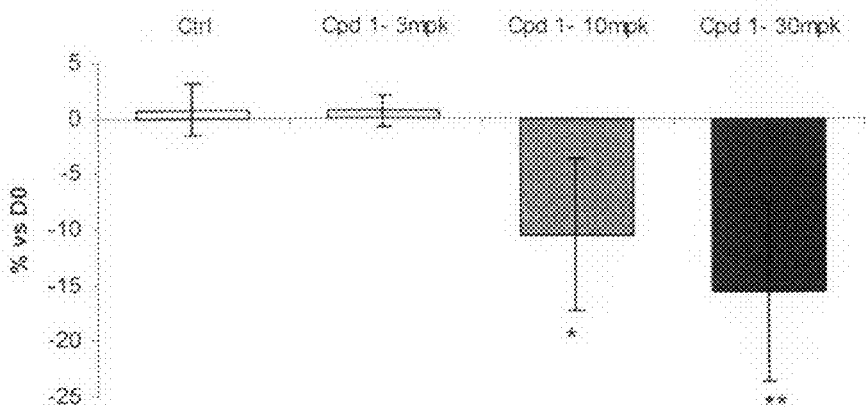
Figures 2, 3:
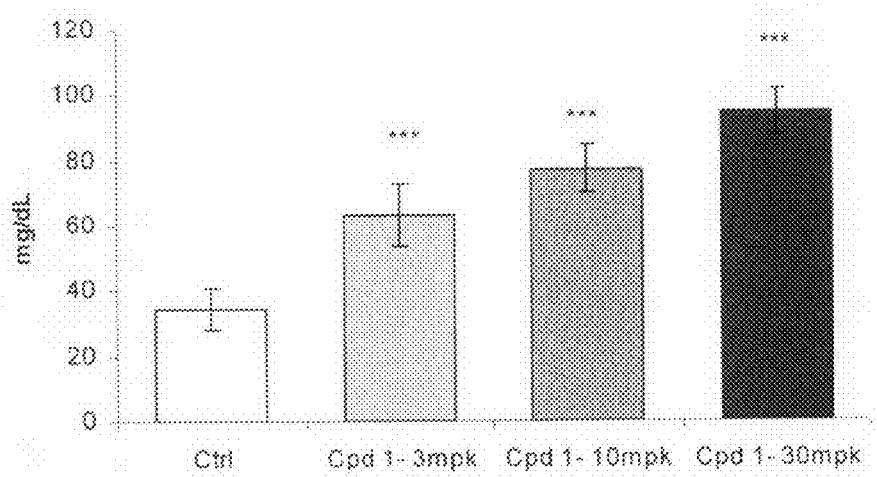
Figure 3:
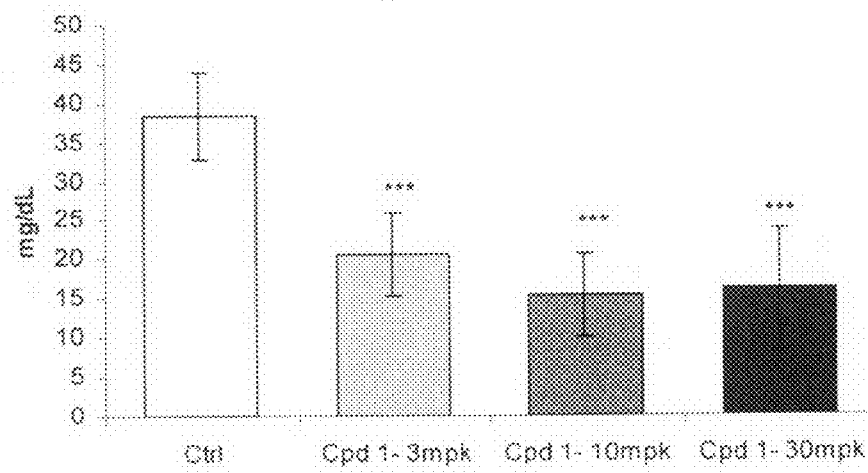
Figures 3, 4:
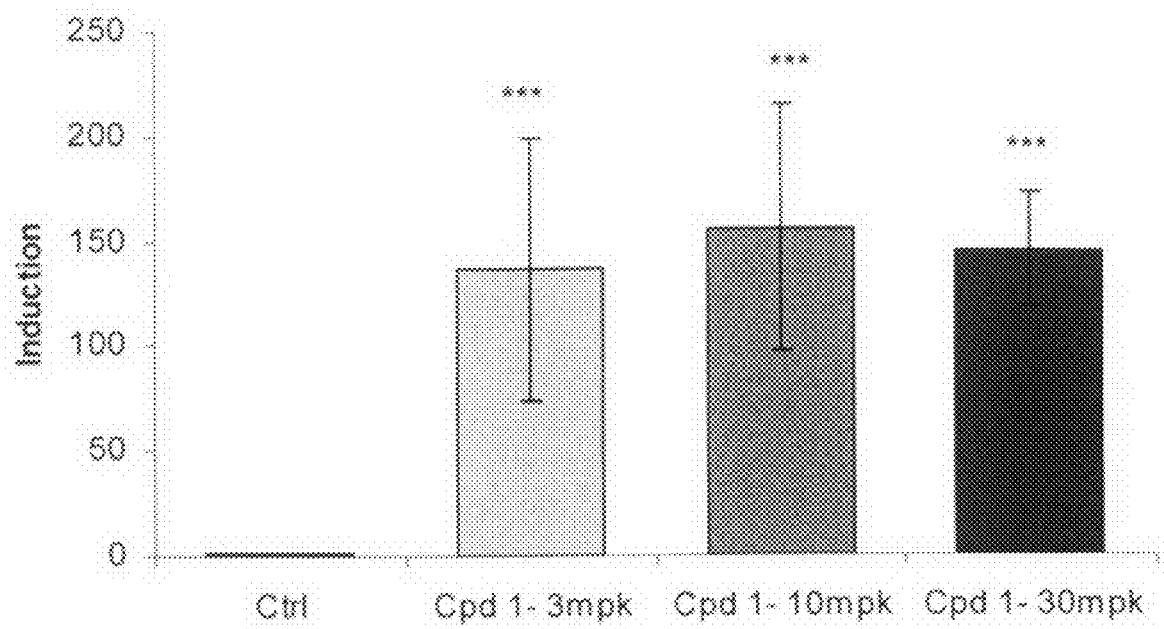
Figures 3, 4, 5:
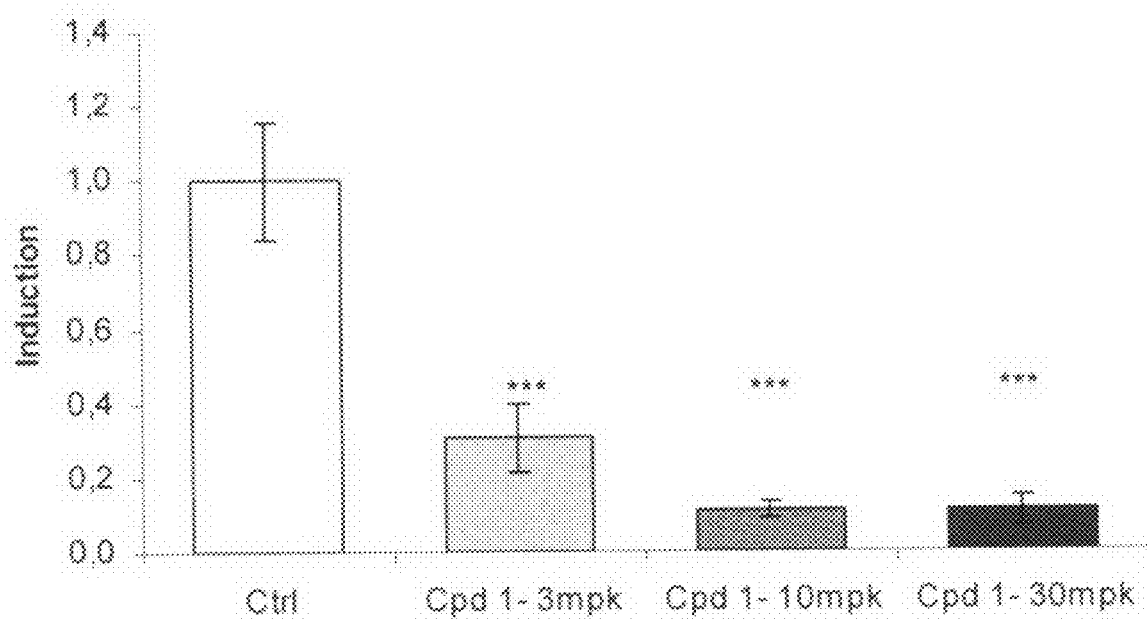
Figures 1, 4:
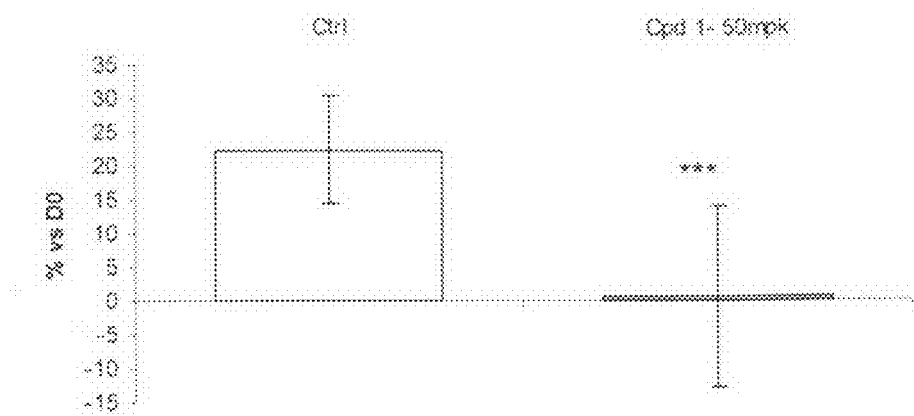
Figures 2, 4:
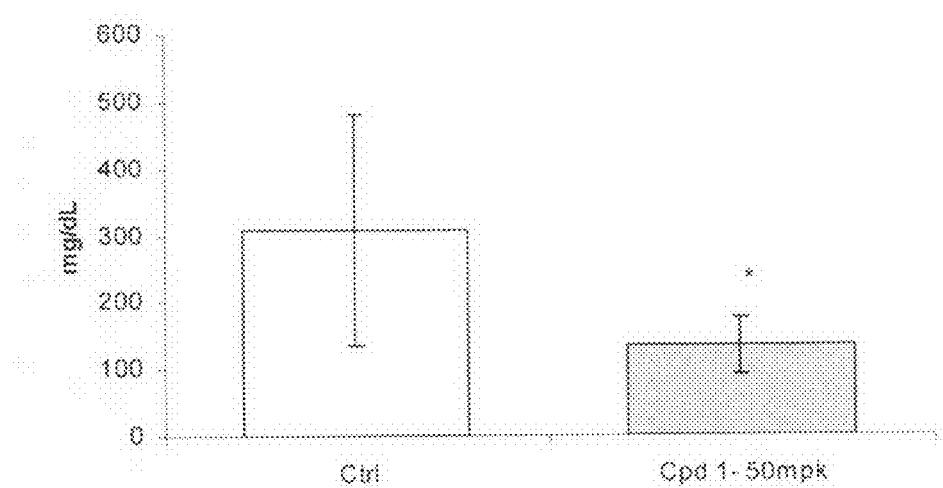
Figures 3, 4:
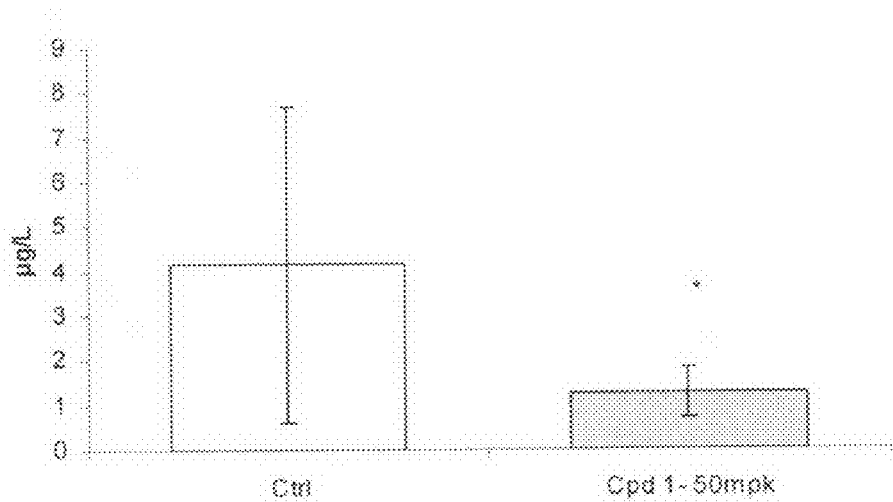
Figure 4:
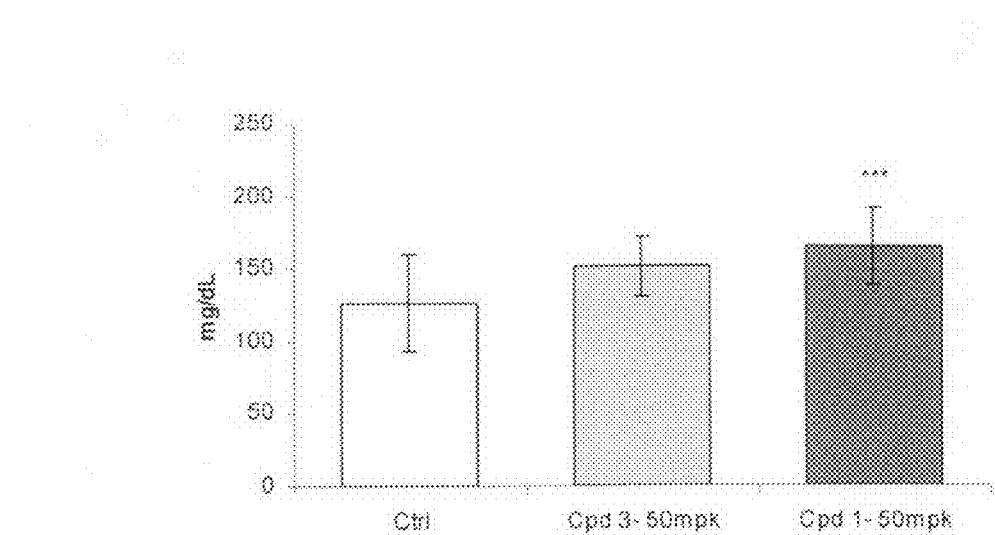
Figures 4, 5:
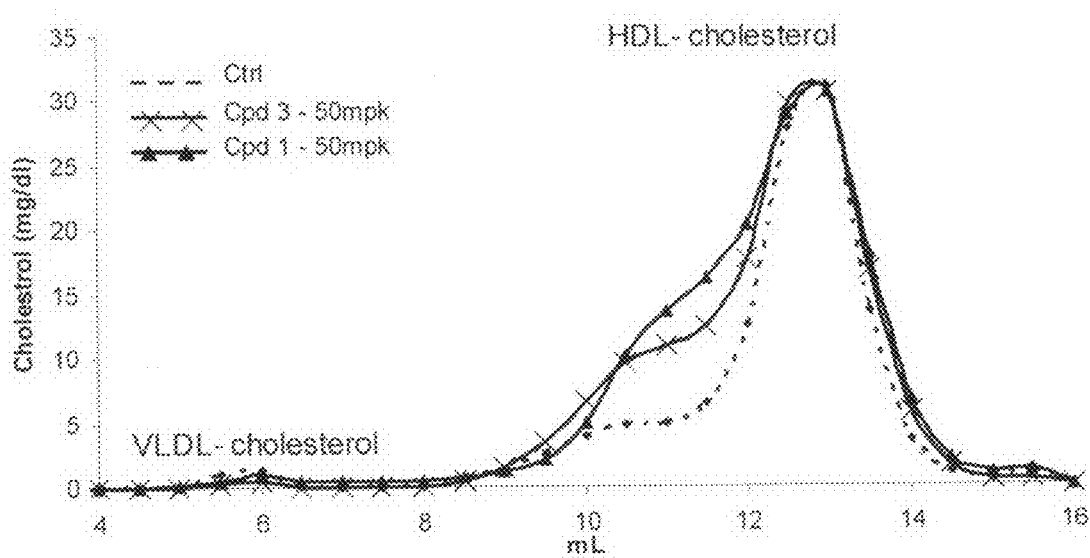
Figures 4, 5, 6:
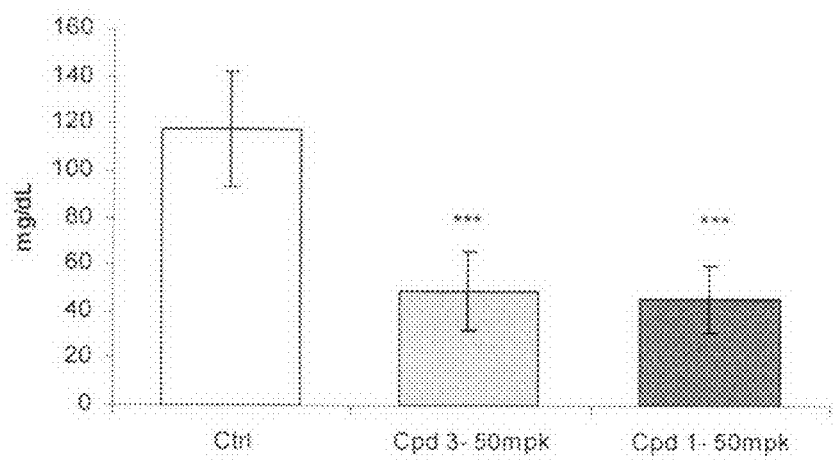
Figures 4, 5, 6, 7:
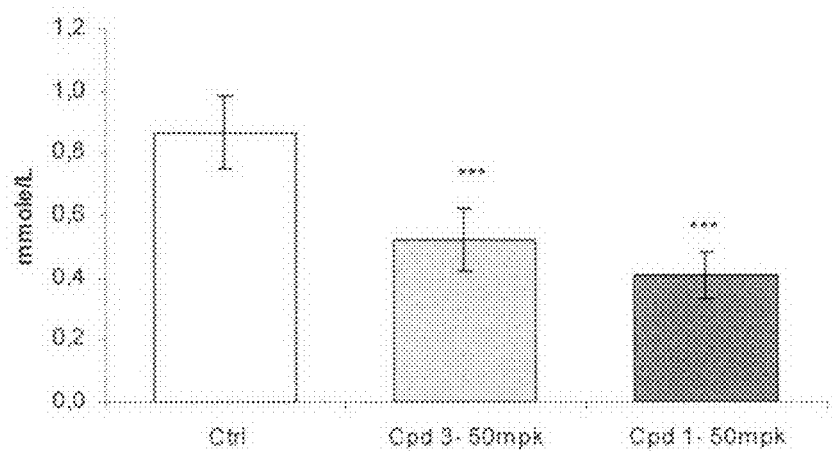
Figures 4, 5, 6, 7, 8:
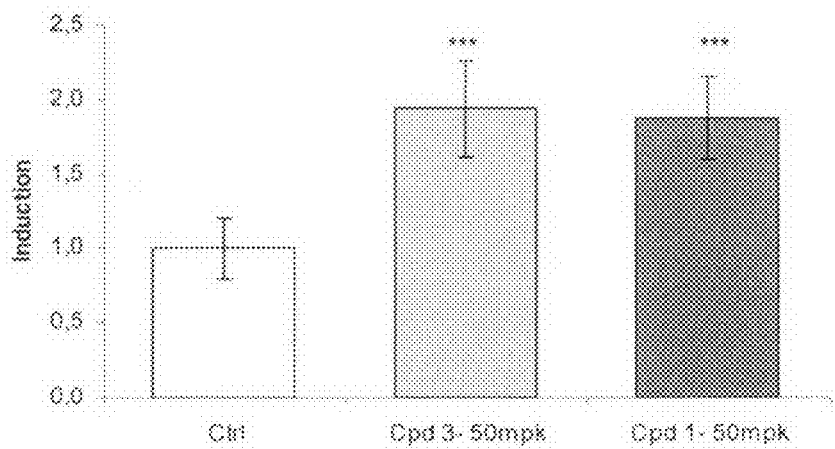
Figures 4, 5, 6, 7, 8, 9:
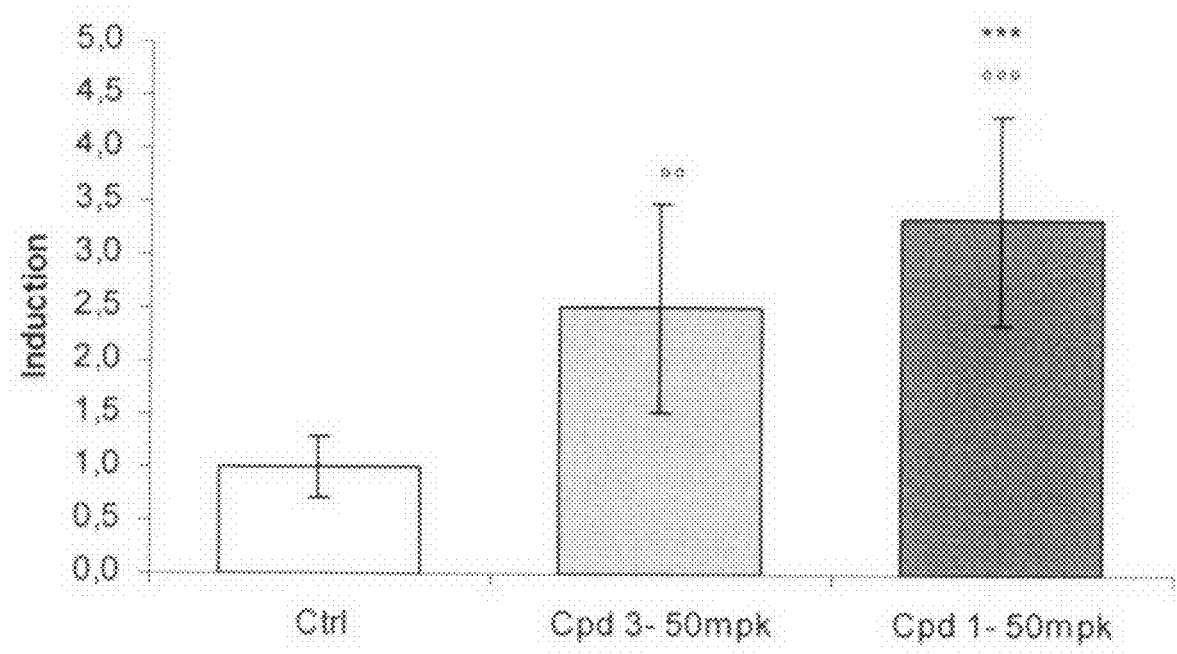
Figure 5:
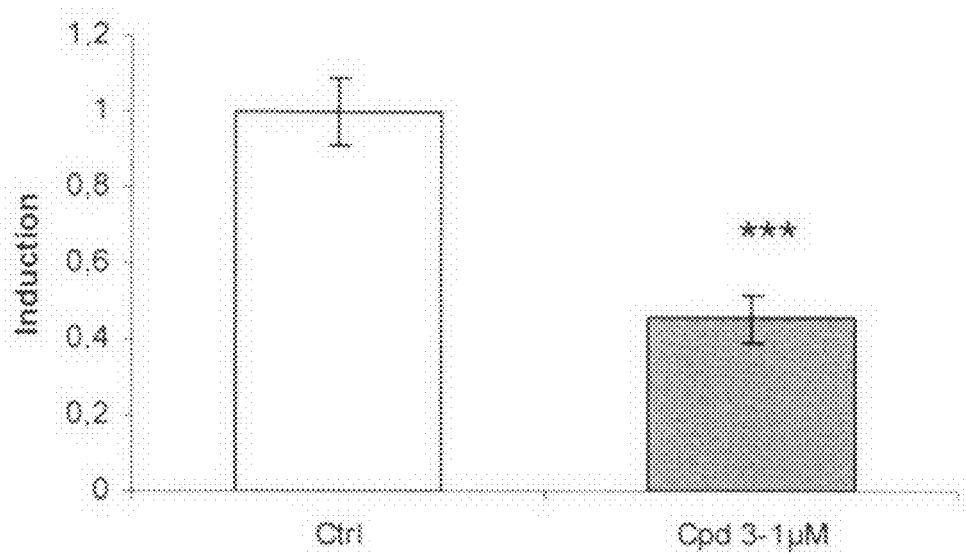

The inventors have also shown that the compounds according to the invention are, in vivo, regulators of PPARs target gene expression. The results presented in FIGS. 3-4 and 3-5 show that compound 1 administered at 3, 10, and 30 mpk for 14 days to C57BI6 mice, induces a significant increase in hepatic expression of the genes coding for PDK4 (FIG. 3-4) and a reduction in hepatic expression of the gene coding for ApoCIII (FIG. 3-5). All the genes coding for enzymes specifically involved in lipid and glucid metabolism and the fact that their expression is modulated by the compounds according to the invention reinforces the idea that these compounds have a great potential for the treatment of metabolic pathologies.

Conclusion

Unexpectedly, the experimental data presented show that the compounds according to the invention, in vivo, induce a body weight loss, stimulate HDL-cholesterol synthesis and have a hypolipidemic effect (reduction of plasma levels of triglycerides). Additionally, the experimental data presented show that the compounds according to the invention modulate the expression of genes regulated by the activation of PPARs that code for enzymes especially involved in lipid and carbohydrate metabolism.

Example 6

In Vivo Evaluation, on the db/db Mouse, of Body-Weight Properties, Antidiabetic Properties, Hypolipidemic Properties, and Properties Stimulating the Synthesis of HDL-Cholesterol of the Compounds According to the Invention Principle The effects of compounds according to the invention on the body weight, insulin resistance, and the hypolipidemic properties of these compounds are evaluated in vivo by measuring the body weight and the rates of plasma glucose and insulin, of plasma lipids, and by analyzing the distribution of cholesterol in different plasma lipoprotein fractions and of the gene expression PPARs target genes after a per os treatment of the db/db mouse with the compounds according to the invention.

Protocol

Treatment of the Animals

Female db/db mice were kept on a 12 hour/12 hour light/dark cycle at a constant temperature of 20±3° C. After a one week acclimatization period, the mice were weighed and divided into groups of 8 animals selected so as to render uniform the distribution of their body weights and their plasma lipid rates, determined before the experiment. The tested compounds were suspended in carboxymethylcellulose (Sigma C4888) and administered intra-gastric tube feeding once a day for 28 days at the chosen dose. The animals had free access to food and water (standard diet). Taking of food and weight gain are recorded throughout the experiment. At the end of the experiment, the animals were anesthetized after a 4 hour fast, a blood sample was taken using (EDTA) anticoagulant, then the mice were weighed and euthanized. The plasma was separated by centrifugation at 3000 rotations/minute for 20 minutes. The samples were kept at +4° C. The hepatic tissue and skeletal muscle tissue samples were taken and frozen immediately in liquid nitrogen then conserved at −80° C. for later analysis.

Measurement of Plasma Glycemia and Insulinemia

Murine plasma glucose is measured out according to an enzyme-colorimetric method using a Glucose RTU kit (Biomérieux). Glucose is transformed into gluconic acid under the action of glucose oxidase; the reaction releases hydrogen peroxide. Hydrogen peroxide is measured according to the Trinder reaction which, under the action of a peroxidase and in the presence of phenol and amino-4-antipyrine, produces water and a colored product, quinoneimine. The color intensity, due to the quinoneimine, is proportional to the amount of glucose present in the sample.

Murine insulin is measured using ELISA method (using the INSKR020 kit from provider Crystal chem.). A microplate is coated with a mouse anti-insulin antibody. Then, the serum to be assayed for insulin is placed onto the plate. A guinea pig anti-insulin antibody is used to recognize the complex formed by the mouse insulin and the anti-insulin monoclonal antibody. Finally an anti-guinea pig antibody labeled with peroxidase is added and bind to the guinea pig anti-insulin antibody. The colorimetric reaction is performed by adding an OPD (ortho phenyl diamine) enzyme substrate. The intensity of the color is proportional to the amount of insulin present in the sample.

Measurement of Plasma Lipids

Plasma lipid concentrations (total cholesterol and triglycerides) are measured by enzymatic assays (bioMérieux-Lyon-France) according to the provider's recommendations.

Analysis of the Distribution of Cholesterol into Plasma Lipoprotein Fractions.

The different lipid fractions (VLDL, LDL, HDL) in the plasma were separated using gel-filtration chromatography. Cholesterol concentrations were then measured for each fraction by enzymatic assays (bioMérieux-Lyon-France) according to the provider's recommendations.

Genetic Expression Analysis by Quantitative RT-PCR

Hepatic Tissue

Total RNA was extracted from liver fragments by using a NucleoSpin® 96 RNA kit (Macherey Nagel, Hoerdt, France) according to the manufacturer's instructions.

Skeletal Tissue

Total RNA was extracted from gastrocnemius skeletal muscle fragments by using a RNeasy® Fibrous Tissue kit (Qiagen) according to the manufacturer's instructions.

1 μg of total RNA (quantified by spectrophotometry) was then reverse-transcripted into complementary DNA by means of a 1 hour reaction at 37° C. in a total volume of 20 μl containing a 1× buffer (Sigma), 1.5 mM of DTT, 0.18 mM of dNTPs (Promega), 200 ng of pdN6 (Amersham), 30 U of RNase inhibitor (Sigma), and 1 μl of MMLV-RT (Sigma).

The PCR quantitative experiments were carried out using the MyiQ Single-Color Real-Time PCR Detection System (Biorad, Marnes-la-Coquette, France) and were performed using the iQ SYBR Green Supermix kit according to the provider's recommendations, in 96-well plates in 5 µl of a diluted reverse-transcription solution at a hybridization temperature of 55° C. The specific primer pairs of the genes being studied were used:

```
                                              (SEQ ID NO: 1)
PDK4: sense primer: 5'-TACTCCACTGCTCCAACACCTG-3'
and (SEQ ID NO: 2))
antisense primer 5'-GTTCTTCGGTTCCCTGCTTG-3'

(SEQ ID NO: 5)
UCP2: sense primer: 5'-GTCGGAGATACCAGAGCACTGTCG-3'
and (SEQ ID NO: 6)
antisense primer 5'-CACATCAACAGGGGAGGCGA-3'
```

The amount of fluorescence emitted is directly proportional to the amount of complementary DNA present at the beginning of the reaction and amplified during the PCR. For each target studied, a range of solutions is performed with successive dilutions of mixtures of a few microliters of different reverse-transcription solutions. The relative levels of expression of each target are thus determined by using efficiency curves obtained with the points relative to the range of PCR solutions.

The expression levels of the genes of interest are then normalized, in the hepatic tissue, regarding the level expression of the reference gene 36B4 (whose specific primers are: sense primer: 5'-CATGCTCAACATCTCCCCCTTCTCC-3' (SEQ ID NO: 7) and antisense primer: 5'-GGGAAGGTG-TAATCCGTCTCCACAG-3' (SEQ ID NO: 8)) and, in skeletal muscle tissue, regarding the expression level of the reference gene 36B4 (whose specific primers are: sense primer: 5'-CGGACACGGACAGGATTGACAG-3' (SEQ ID NO: 9) and antisense primer: 5'-AATCTCGGGTGGCTGAACGC-3' (SEQ ID NO: 10)). The induction factor relative to each sample was then calculated. The higher the induction factor is, the more the compound promotes gene expression. The final result is represented as the average of the induction values within each experimental group.

Results

Body Weight

FIG. 4-1 compares the animals' weight gain after 28 days of treatment with compound 1 administered at 50 mpk to the control animals' weight gain. Unexpectedly, a weight loss was noticed in the animals treated with compound 1.

Measurement of Glycemia and Insulinemia

FIGS. 4-2 and 4-3 compare plasma glucose and insulin levels after 28 days of treatment with compound 1 administered at 50 mpk. Unexpectedly, glycemia and insulinemia are significantly reduced by the treatment.

Measurement of Plasma Lipids

FIG. 4-4 compares the total plasma cholesterol rates after 28 days of treatment with compound 1 and 3, administered at 50 mpk, with the rates obtained from the control animals. Unexpectedly, total cholesterol rates were significantly increased. FIG. 4-5 shows that this increase in total plasma cholesterol corresponds to a significant increase in the HDL-cholesterol fraction induced by the treatment of the animals with compounds 1 and 3 at 50 mpk.

FIGS. 4-6 and 4-7 compare plasma triglyceride and free fatty acid rates after 28 days of treatment with compounds 1 and 3 administered at 50 mpk with the ones obtained from the control animals. Unexpectedly, the circulating triglycerides and free fatty acids rates were very significantly decreased by the treatment.

Gene Expression Analysis by Quantitative RT-PCR

The inventors have also shown that the compounds according to the invention are, in vivo, regulators of PPARs target gene expression. The results presented in FIGS. 4-8 and 4-9 show that compound 1 and 3 administered at 50 mpk for 28 days to the db/db mice, induce a significant increase in hepatic expression of the genes coding for PDK4 (FIG. 4-8) and a reduction of the expression of the gene coding for UCP2 (FIG. 4-9), in the skeletal muscle. All the genes coding for enzymes specifically involved in lipid and glucid metabolism and in energy dissipation, and the fact that their expression is modulated by the compounds according to the invention reinforce the idea that these compounds have a great potential for the treatment of metabolic pathologies.

Conclusion

Unexpectedly, the presented experimental data show that the compounds according to the invention, in vivo, induce a body weight loss and an improvement in insulin sensibility, stimulate HDL-cholesterol synthesis, and has a hypolipidemic effect (leasing to a reduction of plasma triglycerides rates). Additionally, the disclosed experimental data show that the compounds according to the invention modulate the expression of genes, regulated by the activation of PPARs and that code for enzymes especially involved in lipid and glucid metabolism and in energy dissipation.

Example 7

In Vitro Evaluation of the Anti-Inflammatory Properties of the Compounds According to the Invention Principle The anti-inflammatory effects of the compounds according to the invention were evaluated by measuring the secretion of MCP1 (Monocyte chemotactic protein-1) by monocytes treated for 24 hours with compounds according to the invention and stimulated simultaneously with PMA (Phorbol 12-myristate 13-acetate, which promotes an inflammatory response in cells and their differentiation into macrophages). The less MCP-1 is secreted, the more the compound according to the invention inhibits the inflammatory reaction.

Protocol

Culture and Treatment of THP-1 Cells.

The THP-1 human monocytes line (ATCC source) is cultured in a-RPMI1640 medium with 25 mM Hepes (Gibco; 42401-018), 1% glutamine (Gibco; 25030-24) 1% penicillin/streptomycin (Biochrom AG; A 2213), and 10% decomplemented fetal calf serum (SVF. Gibco; 26050-088).

The cells were plated in 24-well plates (Primaria BD Falcon) at a density of 870,000 cells/well then were incubated at 37° C. and 5% $CO_2$ for 24 hours in a culture medium containing 0.2% fetal calf serum in the presence of 5 ng/ml of phorbol 12-myristate 13-acetate (PMA) and 1 µM of compound 3 according to the invention. The compound according to the invention is dissolved in dimethyl sulfoxide (DMSO, Fluka; 41640). The effect of the compounds according to the invention is compared to the effect of the DMSO alone.

Measurement of the Secretion of MCP1

The treatment medium is recovered and the MCP1 concentration is measured using the ELISA kit <<Human MCP-1 ELISA Set>> (BD OptEIA; 555179) in accordance with the manufacturer's recommendation.

MCP1 is laid on a plate and is recognized by an anti-MCP1 specific antibody. This specific antibody is itself specifically recognized by a second antibody coupled with a peroxidase enzyme. The coloration resulting from enzymatic activity is proportional to the quantity of fixed MCP1 and can be measured by a spectrophotometry method. A range is performed from a point representative of a known concentration and from which the MCP1 concentration of each sample is calculated.

The induction factor, i.e. the ratio between the signal induced by the compound according to the invention and the signal induced by the control group, was then calculated. The weaker this factor is, the more the compound inhibits the secretion of MCP1. The final result is represented as the average of the induction values obtained with each experimental group.

Results

The inventors have shown that, on in vitro monocytes, the compounds according to the invention have anti-inflammatory effects. The results presented in FIG. 5 show that compound 3 according to the invention, at 1 μM, induces a significant reduction in MCP1 secreted by monocytes.

Conclusion

Unexpectedly, the disclosed experimental data show that the compounds according to the invention have an anti-inflammatory effect on monocytes stimulated by PMA.

General Conclusion

The inventors have shown that the compounds according to the invention lead to a body weight loss, have hypolipidemic properties, decrease the levels of cholesterol and plasmatic triglycerides, stimulate HDL-cholesterol synthesis, and have antidiabetic properties. Additionally, the inventors have shown that the compounds according to the invention allow a regulation of the expression of genes coding for enzymes specifically involved in lipid and glucid metabolism and in energy dissipation.

The inventors have also shown that the compounds according to the invention have anti-inflammatory properties.

These results, obtained in vivo and in vitro, demonstrate the therapeutic potential of the compounds according to the invention for the treatment of major pathologies such as dyslipidemias, type-2 diabetes, and obesity.

BIBLIOGRAPHY

Fox-Tucker J, *The Cardiovascular Market Outlook to 2010*, BUSINESS INSIGHTS REPORTS, 2005, 1-174

Gross B, et al., *Peroxisome Proliferator-Activated Receptor b/d: A novel target for the reduction of atherosclerosis*, DRUG DISCOVERY TODAY: THERAPEUTIC STRATEGIES, 2005, 2 (3), 237-243

International Atherosclerosis Society, *Harmonized Clinical. Guidelines on Prevention of Atherosclerotic Vascular Disease*, 2003, Kota B P, et al., *An overview on biological mechanisms of PPAR*, Pharmacol Res, 2005, 51 (2), 85-94

Lefebvre P, et al., *Sorting out the roles of PPARalpha in energy metabolism and vascular homeostasis*, J Clin Invest, 2006, 116 (3), 571-580

Lehrke M and Lazar M A, *The many faces of PPARgamma*, Cell, 2005, 123 (6), 993-9

Liu Y and Miller A, *Ligands to peroxisome proliferator-activated receptors as therapeutic options for metabolic syndrome*, DRUG DISCOVERY TODAY: THERAPEUTIC STRATEGIES, 2005, 2 (3), 165-169

Mensah M, *The Atlas of Heart Disease and Stroke*, 2004,

Raspe E, et al., *Modulation of rat liver apolipoprotein gene expression and serum lipid levels by tetradecylthioacetic acid (TTA) via PPAR{alpha} activation*, J. Lipid Res., 1999, 40 (11), 2099-2110

Sullivan P M, et al., Type III hyperlipoproteinemia and spontaneous atherosclerosis in mice resulting from gene replacement of mouse Apoe with human Apoe*2, J Clin Invest, 1998, 102 (1), 130-5.

The invention claimed is:

1. A compound, derived from substituted 1,3-diphenylpropane, having the general formula (I):

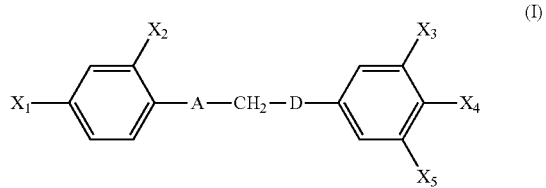

in which:
X1 represents a G1-R1 group;
X2 represents a hydrogen atom;
X3 represents a R3 group;
X4 represents G4-R4 group, wherein R4 represents an alkyl group substituted by one or several group 1 substituents;
X5 represents a R5 group;
R1 representing a halogenated alkyl group;
R3 and R5, identical or different, representing an alkyl group substituted or not by one or several group 1 substituents;
G1 and G4, identical or different, representing an atom of oxygen or sulfur;
A represents:
(i) a —CR6R7 group, in which:
R6 represents a hydrogen atom,
and R7 represents a hydroxy group, or a —OR8 group, R8 representing an alkyl group, substituted or not by an aryl or cycloalkyl group,
(ii) a carbonyl group (CO),
D represents a carbon atom linked to two hydrogen atoms (CH$_2$),
substituents of group 1 are chosen among —COOR9 and —CONR9R10;
R9 and R10, identical or different, representing an atom of hydrogen or an alkyl radical substituted or not by at least one group 1 substituent;
their stereoisomers (diastereoisomers, enantiomers), pure or mixed, racemic mixtures, geometrical isomers, tautomers, salts, solid forms as well as their mixtures.

2. The compound according to claim 1, wherein A represents a carbonyl group (CO), or a stereoisomer, pure or mixed, racemic mixture, geometrical isomer, tautomer, salt, or solid form thereof.

3. The compound according to claim 1, wherein G3, G4, and/or G5 represent an oxygen atom, or a stereoisomer, pure or mixed, racemic mixture, geometrical isomer, tautomer, salt, or solid form thereof.

4. The compound according to claim 1, wherein only one of the X3, X4, and X5 groups corresponds to the formula —OC(CH$_3$)$_2$COOR9, R9 as defined in claim 1, or a stereoisomer, pure or mixed, racemic mixture, geometrical isomer, tautomer, salt, or solid form thereof.

5. The compound according to claim 1, wherein X1 represents a R1 or G1R1 group, G1 as defined in claim 1 and R1 representing a halogenated alkyl group, or a stereoisomer, pure or mixed, racemic mixture, geometrical isomer, tautomer, salt, or solid form thereof.

6. A compound selected from the group consisting of:
2-[2,6-dimethyl-4-[3-[4-(trifluoromethoxy)phenyl]-3-oxo-propyl]phenoxy]-2-methylpropanoic acid,
2-[2,6-dimethyl-4-[3-[4-(trifluoromethylthio)phenyl]-3-oxo-propyl]phenoxy]-2-methylpropanoic acid,
2-[2-methyl-4-[3-[4-(3,3,3-trifluoropropyloxy)phenyl]-3-oxo-propyl]phenoxy]-2-methylpropanoic acid,
2-[2,6-dimethyl-4-[3-hydroxy-3-[4-(trifluoromethylthio)phenyl]propyl]phenoxy]-2-methylpropanoic acid,
2-[2,6-dimethyl-4-(3-(pyridin-3-ylmethoxy)-3-[4-(trifluoromethoxy)phenyl]propyl]phenoxy]-2-methylpropanoic acid,
2-[4-(3-(4-iodobenzyloxy)-3-(4-(trifluoromethoxy)phenyl)propyl)-2,6-diméthylphénoxy]-2-methylpropanoic acid,
2-[4-(3-(4-methoxy)-3-(4-(trifluoromethoxy)phenyl)propyl)-2,6-dimethylphenoxy]-2-methylpropanoic acid,
2-[2,6-dimethyl-4-[3-[4-(3,3,3-trifluoropropyloxy)phenyl]-3-oxo-propyl]phenoxy]-2-methylpropanoic acid,
2-(2,6-dimethyl-4-(3-oxo-3-(4-(2,2,2-trifluoroethoxy)phenyl)propyl)phenoxy)-2-methylpropanoic acid,
2-(2,6-dimethyl-4-(3-oxo-3-(4-(2,2,2-trifluoroethylthio)phenyl)propyl)phenoxy)-2-methylpropanoic acid,
2-(4-(3-(2-fluoro-4-(2,2,2-trifluoroethoxy)phenyl)-3-oxo-propyl)-2,6-dimethylphenoxy)-2-methylpropanoic acid,
2-(2,6-dimethyl-4-(3-(2-methyl-4-(2,2,2-trifluoroethoxy)phenyl)-3-oxo-propyl)phenoxy)-2-methylpropanoic acid,
2-(4-(3-(2-methoxy-4-(2,2,2-trifluoroethoxy)phenyl)-3-oxo-propyl)-2,6-dimethylphenoxy)-2-methylpropanoic acid,
2-(2,6-dimethoxy-4-(3-oxo-3-(4-(trifluoromethoxy)phenyl)propyl)phenoxy)-2-methylpropanoic acid,
2-methyl-2-(2-methyl-4-(3-oxo-3-(4-(trifluoromethylthio)phenyl)propyl)phenoxy)propanoic acid,
2-methyl-2-(2-methyl-4-(3-oxo-3-(4-(trifluoromethoxy)phenyl)propyl)phenoxy)propanoic acid,
2-methyl-2-(3-(3-oxo-3-(4-(trifluoromethoxy)phenyl)propyl)phenoxy)propanoic acid,
2-(2,6-dimethyl-4-(3-oxo-3-(4-(trifluoromethoxy)phenyl)propyl)phenoxy)propanoic acid,
2-[4-(3-hydroxy-3-(4-(trifluoromethoxy)phenyl)propyl)-2,6-dimethylphenoxy]-2-methylpropanoic acid,
2-(2,6-dimethyl-4-(3-oxo-3-(4-(trifluoromethoxy)phenyl)propyl)phenoxy)-2-methylpropanamide, 2-(4-(3-hydroxyimino-3-(4-(trifluoromethoxy)phenyl)propyl)-2,6-dimethylphenoxy)-2-methylpropanoic acid,
2-(4-(3-methoxyimino-3-(4-(trifluoromethoxy)phenyl)propyl)-2,6-dimethylphenoxy)-2-methylpropanoic acid,
4-(2,6-dimethyl-4-(3-oxo-3-(4-(trifluoromethoxy)phenyl)propyl)phenoxy)-2,2-dimethylbutanoic acid,
2-(2,6-dimethyl-4-(3-oxo-3-(4-(trifluoromethoxy)phenyl)propyl)phenoxy)-2-tertiobutyl methylpropanoate,
2-(2,6-dimethyl-4-(3-oxo-3-(4-(trifluoromethoxy)phenyl)propyl)phenoxy)-2-isopropyl methylpropanoate,
2,2-difluoro-2-(2,6-dimethyl-4-(3-oxo-3-(4-(trifluoromethoxy)phenyl)propyl)phenoxy)acetic acid, and
2-(2-methoxy-4-(3-oxo-3-(4-(trifluoromethoxy)phenyl)propyl)phenylthio)-2-methylpropanoic acid, or
a stereoisomer, pure or mixed, racemic mixture, geometrical isomer, tautomer, salt, or solid form thereof.

7. A pharmaceutical composition comprising, in a pharmaceutically acceptable support, at least one compound, stereoisomer, pure or mixed, racemic mixture, geometrical isomer, tautomer, salt, or solid form, as defined in claim 1.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: artificial
<220> FEATURE:
<223> OTHER INFORMATION: sens primer PDK4

<400> SEQUENCE: 1
tactccactg ctccaacacc tg                                          22

<210> SEQ ID NO 2
<211> LENGTH: 20
<212> TYPE: DNA
<213> ORGANISM: artificial
<220> FEATURE:
<223> OTHER INFORMATION: antisens primer PDK4

<400> SEQUENCE: 2
gttcttcggt tccctgcttg                                             20

<210> SEQ ID NO 3
<211> LENGTH: 20
<212> TYPE: DNA
<213> ORGANISM: artificial

```
<220> FEATURE:
<223> OTHER INFORMATION: sens primer ApoCIII

<400> SEQUENCE: 3
ctcttggctc tcctggcatc                                              20

<210> SEQ ID NO 4
<211> LENGTH: 20
<212> TYPE: DNA
<213> ORGANISM: artificial
<220> FEATURE:
<223> OTHER INFORMATION: antisens primer ApoCIII

<400> SEQUENCE: 4
gcatcctgga ccgtcttgga                                              20

<210> SEQ ID NO 5
<211> LENGTH: 24
<212> TYPE: DNA
<213> ORGANISM: artificial
<220> FEATURE:
<223> OTHER INFORMATION: sens primer UCP2

<400> SEQUENCE: 5
gtcggagata ccagagcact gtcg                                         24

<210> SEQ ID NO 6
<211> LENGTH: 20
<212> TYPE: DNA
<213> ORGANISM: artificial
<220> FEATURE:
<223> OTHER INFORMATION: antisens primer UCP2

<400> SEQUENCE: 6
cacatcaaca ggggaggcga                                              20

<210> SEQ ID NO 7
<211> LENGTH: 25
<212> TYPE: DNA
<213> ORGANISM: artificial
<220> FEATURE:
<223> OTHER INFORMATION: sens primer 36B4

<400> SEQUENCE: 7
catgctcaac atctccccct tctcc                                        25

<210> SEQ ID NO 8
<211> LENGTH: 25
<212> TYPE: DNA
<213> ORGANISM: artificial
<220> FEATURE:
<223> OTHER INFORMATION: antisens primer 36B4

<400> SEQUENCE: 8
gggaaggtgt aatccgtctc cacag                                        25

<210> SEQ ID NO 9
<211> LENGTH: 22
<212> TYPE: DNA
<213> ORGANISM: artificial
<220> FEATURE:
<223> OTHER INFORMATION: sens primer 18S

<400> SEQUENCE: 9
cggacacgga caggattgac ag                                           22
```

```
<210> SEQ ID NO 10
<211> LENGTH: 20
<212> TYPE: DNA
<213> ORGANISM: artificial
<220> FEATURE:
<223> OTHER INFORMATION: antisens primer 18S

<400> SEQUENCE: 10
aatctcgggt ggctgaacgc                                              20
```